United States Patent
Fierens et al.

(10) Patent No.: US 9,517,146 B2
(45) Date of Patent: Dec. 13, 2016

(54) METHODS AND APPARATUS FOR STENTING COMPRISING ENHANCED EMBOLIC PROTECTION COUPLED WITH IMPROVED PROTECTIONS AGAINST RESTENOSIS AND THROMBUS FORMATION

(71) Applicant: Abbott Laboratories Vascular Enterprises Limited, Dublin (IE)

(72) Inventors: Joost J. Fierens, Dworp (BE); Silvio R. Schaffner, Berlingen (CH); Marc Gregory Gianotti, Wiesendangen (CH); Gerd Seibold, Ammerbuch (DE); Randolf von Oepen, Aptos, CA (US)

(73) Assignee: ABBOTT LABORATORIES VASCULAR ENTERPRISES LIMITED, Dublin (IE)

(*) Notice: Subject to any disclaimer, the term of this patent is extended or adjusted under 35 U.S.C. 154(b) by 142 days.

(21) Appl. No.: 14/323,658

(22) Filed: Jul. 3, 2014

(65) Prior Publication Data
US 2014/0324157 A1 Oct. 30, 2014

Related U.S. Application Data

(63) Continuation of application No. 13/089,039, filed on Apr. 18, 2011, now Pat. No. 8,814,926, which is a
(Continued)

(30) Foreign Application Priority Data

Sep. 5, 1998 (DE) .................... 184 00 645

(51) Int. Cl.
*A61F 2/07* (2013.01)
*A61F 2/856* (2013.01)
(Continued)

(52) U.S. Cl.
CPC ............. *A61F 2/856* (2013.01); *A61F 2/07* (2013.01); *A61F 2/82* (2013.01); *A61F 2/91* (2013.01);
(Continued)

(58) Field of Classification Search
None
See application file for complete search history.

(56) References Cited

U.S. PATENT DOCUMENTS 4,475,972 A 10/1984 Wong
4,580,568 A 4/1986 Gianturco
(Continued)

FOREIGN PATENT DOCUMENTS

CA 2309079 11/2004
EP 0357003 3/1990
(Continued)

OTHER PUBLICATIONS

U.S. Appl. No. 60/637,495, filed Dec. 20, 2004, Fierens et al.
(Continued)

*Primary Examiner* — Yashita Sharma
*Assistant Examiner* — Rebecca Preston
(74) *Attorney, Agent, or Firm* — Workman Nydegger; John Kwok

(57) ABSTRACT

Apparatus and methods for stenting are provided comprising a stent attached to a porous biocompatible material that is permeable to endothelial cell ingrowth, but impermeable to release of emboli of predetermined size. Preferred stent designs are provided, as well as preferred manufacturing techniques. Apparatus and methods are also provided for use at a vessel branching. Moreover, embodiments of the present invention may comprise a coating configured for localized delivery of therapeutic agents. Embodiments of the present invention are expected to provide enhanced embolic protec-
(Continued)

tion, improved force distribution, and improved recrossability, while reducing a risk of restenosis and thrombus formation.

20 Claims, 11 Drawing Sheets

Related U.S. Application Data continuation of application No. 11/731,820, filed on Mar. 29, 2007, now Pat. No. 7,927,365, which is a continuation of application No. 10/859,636, filed on Jun. 3, 2004, now Pat. No. 7,927,364, which is a continuation of application No. 09/967,789, filed on Sep. 28, 2001, now Pat. No. 6,755,856, which is a continuation-in-part of application No. 09/742,144, filed on Dec. 19, 2000, now Pat. No. 6,682,554, which is a continuation-in-part of application No. 09/582,318, filed as application No. PCT/EP99/06456 on Sep. 2, 1999, now Pat. No. 6,602,285.

(51) Int. Cl.
*A61F 2/91* (2013.01)
*A61F 2/915* (2013.01)
*A61F 2/82* (2013.01)
*A61F 2/00* (2006.01)
*A61F 2/90* (2013.01)

(52) U.S. Cl.
CPC ............ *A61F 2/915* (2013.01); *A61F 2/90* (2013.01); *A61F 2002/0086* (2013.01); *A61F 2002/91508* (2013.01); *A61F 2002/91533* (2013.01); *A61F 2002/91558* (2013.01); *A61F 2220/005* (2013.01); *A61F 2220/0008* (2013.01); *A61F 2220/0016* (2013.01)

(56) References Cited

U.S. PATENT DOCUMENTS

| | | | |
|---|---|---|---|
| 4,738,740 A | 4/1988 | Pinchuk et al. |
| 4,743,252 A | 5/1988 | Martin, Jr. et al. |
| 4,759,757 A | 7/1988 | Pinchuk |
| 4,776,337 A | 10/1988 | Palmaz |
| 4,800,882 A | 1/1989 | Gianturco |
| 4,907,336 A | 3/1990 | Gianturco |
| 5,015,253 A | 5/1991 | MacGregor |
| 5,019,090 A | 5/1991 | Pinchuk |
| 5,041,126 A | 8/1991 | Gianturco |
| 5,053,048 A | 10/1991 | Pinchuk |
| 5,059,211 A | 10/1991 | Stack et al. |
| 5,102,417 A | 4/1992 | Palmaz |
| 5,104,404 A | 4/1992 | Wolff |
| 5,116,360 A | 5/1992 | Pinchuk et al. |
| 5,122,154 A | 6/1992 | Rhodes |
| 5,133,732 A | 7/1992 | Wiktor |
| 5,147,370 A | 9/1992 | McNamara et al. |
| 5,163,951 A | 11/1992 | Pinchuk et al. |
| 5,171,262 A | 12/1992 | MacGregor |
| 5,221,261 A | 6/1993 | Termin et al. |
| 5,282,823 A | 2/1994 | Schwartz et al. |
| 5,292,331 A | 3/1994 | Boneau |
| 5,314,444 A | 5/1994 | Gianturco |
| 5,370,683 A | 12/1994 | Fontaine |
| 5,378,239 A | 1/1995 | Termin et al. |
| 5,380,299 A | 1/1995 | Fearnot et al. |
| 5,421,955 A | 6/1995 | Lau et al. |
| 5,443,458 A | 8/1995 | Eury |
| 5,443,496 A | 8/1995 | Schwartz et al. |
| 5,449,373 A | 9/1995 | Pinchasik et al. |
| 5,449,382 A | 9/1995 | Dayton |
| 5,476,508 A | 12/1995 | Amstrup |
| 5,496,277 A | 3/1996 | Termin et al. |
| 5,514,154 A | 5/1996 | Lau et al. |
| 5,527,354 A | 6/1996 | Fontaine et al. |
| 5,556,414 A | 9/1996 | Turi |
| 5,569,295 A | 10/1996 | Lam |
| 5,591,197 A | 1/1997 | Orth et al. |
| 5,591,224 A | 1/1997 | Schwartz et al. |
| 5,593,417 A | 1/1997 | Rhodes |
| 5,593,442 A | 1/1997 | Klein |
| 5,603,721 A | 2/1997 | Lau et al. |
| 5,609,606 A | 3/1997 | O'Boyle |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,649,952 A | 7/1997 | Lam |
| 5,651,174 A | 7/1997 | Schwartz et al. |
| 5,653,747 A | 8/1997 | Dereume |
| 5,670,161 A | 9/1997 | Healy et al. |
| 5,674,242 A | 10/1997 | Phan et al. |
| 5,674,277 A | 10/1997 | Freitag |
| 5,693,085 A | 12/1997 | Buirge et al. |
| 5,695,516 A | 12/1997 | Fischell et al. |
| 5,697,971 A | 12/1997 | Fischell et al. |
| 5,700,285 A | 12/1997 | Myers et al. |
| 5,707,386 A | 1/1998 | Schnepp-Pesch et al. |
| 5,707,388 A | 1/1998 | Lauterjung |
| 5,709,703 A | 1/1998 | Lukic et al. |
| 5,709,713 A | 1/1998 | Evans et al. |
| 5,716,393 A | 2/1998 | Lindenburg et al. |
| 5,723,003 A | 3/1998 | Winston et al. |
| 5,723,004 A | 3/1998 | Dereume et al. |
| 5,728,158 A | 3/1998 | Lau et al. |
| 5,733,303 A | 3/1998 | Israel et al. |
| 5,735,892 A | 4/1998 | Myers et al. |
| 5,735,893 A | 4/1998 | Lau et al. |
| 5,735,897 A | 4/1998 | Buirge |
| 5,738,817 A | 4/1998 | Danforth et al. |
| 5,741,325 A | 4/1998 | Chaikof et al. |
| 5,741,327 A | 4/1998 | Frantzen |
| 5,743,874 A | 4/1998 | Fischell et al. |
| 5,749,880 A | 5/1998 | Banas et al. |
| 5,755,771 A | 5/1998 | Penn et al. |
| 5,755,772 A | 5/1998 | Evans et al. |
| 5,755,774 A | 5/1998 | Pinchuk |
| 5,755,781 A | 5/1998 | Jayaraman |
| 5,769,884 A | 6/1998 | Solovay |
| 5,776,161 A | 7/1998 | Globerman |
| 5,776,181 A | 7/1998 | Lee et al. |
| 5,776,183 A | 7/1998 | Kanesaka et al. |
| 5,782,904 A | 7/1998 | White et al. |
| 5,800,526 A | 9/1998 | Anderson et al. |
| 5,807,404 A | 9/1998 | Richter |
| 5,810,868 A | 9/1998 | Lashinski et al. |
| 5,810,870 A | 9/1998 | Myers et al. |
| 5,810,872 A | 9/1998 | Kanesaka et al. |
| 5,814,063 A | 9/1998 | Freitag |
| 5,817,126 A | 10/1998 | Imran |
| 5,824,037 A | 10/1998 | Fogarty et al. |
| 5,824,045 A | 10/1998 | Alt |
| 5,824,048 A | 10/1998 | Tuch |
| 5,824,054 A | 10/1998 | Khosravi et al. |
| 5,824,059 A | 10/1998 | Wijay |
| 5,827,321 A | 10/1998 | Roubin et al. |
| 5,836,964 A | 11/1998 | Richter et al. |
| 5,836,966 A | 11/1998 | St. Germain |
| 5,843,120 A | 12/1998 | Israel et al. |
| 5,843,158 A | 12/1998 | Lenker et al. |
| 5,843,161 A | 12/1998 | Solovay |
| 5,843,164 A | 12/1998 | Frantzen et al. |
| 5,846,247 A | 12/1998 | Unsworth et al. |
| 5,853,419 A | 12/1998 | Imran |
| 5,855,598 A | 1/1999 | Pinchuk |
| 5,855,600 A | 1/1999 | Alt |
| 5,860,999 A | 1/1999 | Schnepp-Pesch et al. |
| 5,861,027 A | 1/1999 | Trapp |
| 5,868,781 A | 2/1999 | Killion |
| 5,871,538 A | 2/1999 | Dereume |
| 5,876,449 A | 3/1999 | Starck et al. |

(56) References Cited

U.S. PATENT DOCUMENTS

| | | |
|---|---|---|
| 5,876,450 A | 3/1999 | Johlin, Jr. |
| 5,895,406 A | 4/1999 | Gray et al. |
| 5,897,589 A | 4/1999 | Cottenceau et al. |
| 5,922,021 A | 7/1999 | Jang |
| 5,928,248 A | 7/1999 | Acker |
| 5,938,682 A | 8/1999 | Hojeibane et al. |
| 5,948,016 A | 9/1999 | Jang |
| 5,948,018 A | 9/1999 | Dereume et al. |
| 5,954,743 A | 9/1999 | Jang |
| 5,968,091 A | 10/1999 | Pinchuk et al. |
| 5,968,561 A | 10/1999 | Batchelder et al. |
| 5,980,552 A | 11/1999 | Pinchasik et al. |
| 5,984,965 A | 11/1999 | Knapp et al. |
| 6,017,365 A | 1/2000 | Von Oepen |
| 6,019,789 A | 2/2000 | Dinh et al. |
| 6,027,526 A | 2/2000 | Limon et al. |
| 6,033,433 A | 3/2000 | Ehr et al. |
| 6,033,434 A | 3/2000 | Borghi |
| 6,033,435 A | 3/2000 | Penn et al. |
| 6,039,756 A | 3/2000 | Jang |
| 6,042,597 A | 3/2000 | Kveen et al. |
| 6,048,361 A | 4/2000 | Von Oepen |
| 6,056,767 A | 5/2000 | Boussignac et al. |
| 6,059,811 A | 5/2000 | Pinchasik et al. |
| 6,068,656 A | 5/2000 | Von Oepen |
| 6,071,308 A | 6/2000 | Ballou et al. |
| 6,086,610 A | 7/2000 | Duerig et al. |
| 6,099,561 A | 8/2000 | Alt |
| 6,106,548 A | 8/2000 | Roubin et al. |
| 6,113,627 A | 9/2000 | Jang |
| 6,117,165 A | 9/2000 | Becker |
| 6,117,535 A | 9/2000 | Szycher et al. |
| 6,123,721 A | 9/2000 | Jang |
| 6,132,460 A | 10/2000 | Thompson |
| 6,136,023 A | 10/2000 | Boyle |
| 6,152,957 A | 11/2000 | Jang |
| 6,165,212 A | 12/2000 | Dereume et al. |
| 6,168,409 B1 | 1/2001 | Fare |
| 6,174,326 B1 | 1/2001 | Kitaoka et al. |
| 6,179,868 B1 | 1/2001 | Burpee et al. |
| 6,190,403 B1 | 2/2001 | Fischell et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,335 B1 | 3/2001 | Igaki |
| 6,203,569 B1 | 3/2001 | Wijay |
| 6,210,429 B1 | 4/2001 | Vardi et al. |
| 6,231,598 B1 | 5/2001 | Berry et al. |
| 6,231,600 B1 | 5/2001 | Zhong |
| 6,241,762 B1 | 6/2001 | Shanley |
| 6,245,101 B1 | 6/2001 | Drasler et al. |
| 6,253,443 B1 | 7/2001 | Johnson |
| 6,258,115 B1 | 7/2001 | Dubrul |
| 6,258,116 B1 | 7/2001 | Hojeibane |
| 6,261,318 B1 | 7/2001 | Lee et al. |
| 6,261,319 B1 | 7/2001 | Kveen et al. |
| 6,264,688 B1 | 7/2001 | Herklotz et al. |
| 6,264,690 B1 | 7/2001 | Von Oepen |
| 6,270,524 B1 | 8/2001 | Kim |
| 6,273,913 B1 | 8/2001 | Wright et al. |
| 6,299,604 B1 | 10/2001 | Ragheb et al. |
| 6,299,635 B1 | 10/2001 | Frantzen |
| 6,325,825 B1 | 12/2001 | Kula et al. |
| 6,331,189 B1 | 12/2001 | Wolinsky et al. |
| 6,332,089 B1 | 12/2001 | Acker et al. |
| 6,340,366 B2 | 1/2002 | Wijay |
| 6,348,065 B1 | 2/2002 | Brown et al. |
| 6,377,835 B1 | 4/2002 | Schoenberg et al. |
| 6,395,020 B1 | 5/2002 | Ley et al. |
| 6,416,539 B1 | 7/2002 | Hassdenteufel |
| 6,436,132 B1 | 8/2002 | Patel et al. |
| 6,443,982 B1 | 9/2002 | Israel et al. |
| 6,451,049 B2 | 9/2002 | Vallana et al. |
| 6,485,508 B1 | 11/2002 | McGuinness |
| 6,488,702 B1 | 12/2002 | Besselink |
| 6,491,718 B1 | 12/2002 | Ahmad |
| 6,503,272 B2 | 1/2003 | Duerig et al. |
| 6,506,211 B1 | 1/2003 | Skubitz et al. |
| 6,508,834 B1 | 1/2003 | Pinchasik et al. |
| 6,540,776 B2 | 4/2003 | Sanders Millare et al. |
| 6,558,415 B2 | 5/2003 | Thompson |
| 6,562,065 B1 | 5/2003 | Shanley |
| 6,572,646 B1 | 6/2003 | Boylan et al. |
| 6,589,276 B2 | 7/2003 | Pinchasik et al. |
| 6,602,281 B1 | 8/2003 | Klein |
| 6,602,285 B1 | 8/2003 | Von Oepen et al. |
| 6,607,554 B2 | 8/2003 | Dang et al. |
| 6,616,689 B1 | 9/2003 | Ainsworth et al. |
| 6,624,097 B2 | 9/2003 | Martin et al. |
| D481,139 S | 10/2003 | Seibold et al. |
| 6,629,994 B2 | 10/2003 | Gomez et al. |
| 6,652,574 B1 | 11/2003 | Jayaraman |
| 6,676,701 B2 | 1/2004 | Rourke et al. |
| 6,679,911 B2 | 1/2004 | Burgermeister |
| 6,682,554 B2 | 1/2004 | Oepen et al. |
| 6,723,119 B2 | 4/2004 | Pinchasik et al. |
| 6,730,116 B1 | 5/2004 | Wolinsky et al. |
| 6,730,252 B1 | 5/2004 | Teoh et al. |
| 6,740,114 B2 | 5/2004 | Burgermeister |
| 6,749,629 B1 | 6/2004 | Hong et al. |
| 6,755,856 B2 | 6/2004 | Fierens et al. |
| 6,761,733 B2 | 7/2004 | Chobotov et al. |
| 6,770,088 B1 | 8/2004 | Jang |
| 6,776,793 B2 | 8/2004 | Brown et al. |
| 6,776,794 B1 | 8/2004 | Hong et al. |
| 6,786,922 B2 | 9/2004 | Schaeffer |
| 6,790,226 B2 | 9/2004 | Edwin et al. |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 | 4/2005 | Pinchasik et al. |
| 6,881,222 B2 | 4/2005 | White et al. |
| 6,896,697 B1 | 5/2005 | Yip et al. |
| 6,913,619 B2 | 7/2005 | Brown et al. |
| 6,916,336 B2 | 7/2005 | Patel et al. |
| 6,929,660 B1 | 8/2005 | Ainsworth et al. |
| 6,942,689 B2 | 9/2005 | Majercak |
| 6,955,686 B2 | 10/2005 | Majercak et al. |
| 6,998,060 B2 | 2/2006 | Tomonto |
| 7,029,493 B2 | 4/2006 | Majercak et al. |
| 7,060,088 B1 | 6/2006 | Fischell et al. |
| 7,060,093 B2 | 6/2006 | Dang et al. |
| 7,070,614 B1 | 7/2006 | Neuss et al. |
| 7,128,756 B2 | 10/2006 | Lowe et al. |
| 7,141,062 B1 | 11/2006 | Pinchasik et al. |
| 7,179,286 B2 | 2/2007 | Lenz |
| 7,204,848 B1 | 4/2007 | Brown et al. |
| 7,329,277 B2 | 2/2008 | Addonizio et al. |
| 7,520,892 B1 | 4/2009 | Ainsworth et al. |
| 7,611,531 B2 | 11/2009 | Calisse |
| 7,625,398 B2 | 12/2009 | Clifford et al. |
| 7,686,843 B2 | 3/2010 | Moore |
| 7,766,956 B2 | 8/2010 | Jang |
| 7,789,904 B2 | 9/2010 | Von Oepen et al. |
| 7,789,905 B2 | 9/2010 | Oepen et al. |
| 7,794,491 B2 | 9/2010 | Von Oepen et al. |
| 7,811,314 B2 | 10/2010 | Fierens et al. |
| 7,815,672 B2 | 10/2010 | Von Oepen et al. |
| 7,815,763 B2 | 10/2010 | Fierens et al. |
| 7,842,078 B2 | 11/2010 | Von Oepen et al. |
| 7,842,079 B2 | 11/2010 | Von Oepen et al. |
| 7,846,196 B2 | 12/2010 | Von Oepen et al. |
| 7,850,726 B2 | 12/2010 | Casey |
| 7,887,577 B2 | 2/2011 | Von Oepen et al. |
| 7,887,578 B2 | 2/2011 | Schneider |
| 7,927,364 B2 | 4/2011 | Fierens et al. |
| 7,927,365 B2 | 4/2011 | Fierens et al. |
| 8,016,874 B2 | 9/2011 | Casey |
| 8,034,097 B2 | 10/2011 | Neuss et al. |
| 8,088,157 B2 | 1/2012 | Fierens et al. |
| 8,128,679 B2 | 3/2012 | Casey |
| 8,246,674 B2 | 8/2012 | Casey |
| 8,303,645 B2 | 11/2012 | Von Oepen et al. |

(56) References Cited

U.S. PATENT DOCUMENTS

| | | | |
|---|---|---|---|
| 8,337,544 B2 | 12/2012 | Osman et al. | |
| 8,343,208 B2 | 1/2013 | Schneider | |
| 2001/0007955 A1 | 7/2001 | Drasler et al. | |
| 2001/0020183 A1* | 9/2001 | Jang | A61F 2/91 623/1.15 |
| 2001/0027339 A1 | 10/2001 | Boatman et al. | |
| 2001/0049549 A1 | 12/2001 | Boylan et al. | |
| 2002/0019660 A1 | 2/2002 | Gianotti et al. | |
| 2002/0042647 A1 | 4/2002 | Jang | |
| 2002/0055770 A1 | 5/2002 | Doran et al. | |
| 2002/0058990 A1 | 5/2002 | Jang | |
| 2002/0065549 A1 | 5/2002 | White et al. | |
| 2002/0107560 A1 | 8/2002 | Richter | |
| 2002/0111669 A1 | 8/2002 | Pazienza et al. | |
| 2002/0113331 A1 | 8/2002 | Zhang et al. | |
| 2002/0151964 A1 | 10/2002 | Smith et al. | |
| 2002/0169499 A1 | 11/2002 | Zilla et al. | |
| 2003/0055487 A1 | 3/2003 | Calisse | |
| 2003/0083736 A1 | 5/2003 | Brown et al. | |
| 2003/0114918 A1 | 6/2003 | Garrison et al. | |
| 2003/0120334 A1 | 6/2003 | Gerberding | |
| 2004/0002753 A1 | 1/2004 | Burgermeister et al. | |
| 2004/0024445 A1 | 2/2004 | Dickson | |
| 2004/0051201 A1 | 3/2004 | Greenhalgh et al. | |
| 2004/0093073 A1 | 5/2004 | Lowe et al. | |
| 2004/0102836 A1 | 5/2004 | Fischell et al. | |
| 2004/0126405 A1 | 7/2004 | Sahatjian et al. | |
| 2004/0133271 A1 | 7/2004 | Jang | |
| 2004/0167615 A1 | 8/2004 | Lenz | |
| 2004/0230293 A1 | 11/2004 | Yip et al. | |
| 2004/0243220 A1 | 12/2004 | Gianotti et al. | |
| 2004/0267353 A1 | 12/2004 | Gregorich | |
| 2005/0075716 A1 | 4/2005 | Yan | |
| 2005/0222671 A1 | 10/2005 | Schaeffer et al. | |
| 2006/0015173 A1 | 1/2006 | Clifford et al. | |
| 2006/0106452 A1 | 5/2006 | Niermann | |
| 2006/0142844 A1 | 6/2006 | Lowe et al. | |
| 2006/0184232 A1 | 8/2006 | Gianotti et al. | |
| 2006/0247759 A1 | 11/2006 | Burpee et al. | |
| 2007/0021827 A1 | 1/2007 | Lowe et al. | |
| 2007/0299505 A1 | 12/2007 | Gregorich et al. | |
| 2008/0077231 A1 | 3/2008 | Heringes et al. | |
| 2008/0221664 A1 | 9/2008 | Bales et al. | |
| 2009/0163996 A1 | 6/2009 | Bregulla | |
| 2009/0163998 A1 | 6/2009 | Casey | |
| 2009/0264986 A1 | 10/2009 | Bales et al. | |
| 2010/0057190 A1 | 3/2010 | Issenmann | |
| 2010/0114297 A1 | 5/2010 | Calisse | |
| 2010/0249903 A1 | 9/2010 | Wack et al. | |
| 2011/0022159 A1 | 1/2011 | Fierens et al. | |
| 2011/0270381 A1 | 11/2011 | Fierens et al. | |
| 2012/0165921 A1 | 6/2012 | Casey | |
| 2012/0277844 A1 | 11/2012 | Wu | |
| 2013/0190856 A1 | 7/2013 | Von Oepen et al. | |
| 2013/0218254 A1 | 8/2013 | Cattaneo et al. | |
| 2013/0268055 A1 | 10/2013 | Cottone | |
| 2014/0277383 A1 | 9/2014 | Sachar et al. | |

FOREIGN PATENT DOCUMENTS

| | | |
|---|---|---|
| EP | 0221570 | 1/1991 |
| EP | 0565251 | 10/1993 |
| EP | 0699451 | 3/1996 |
| EP | 0709067 | 5/1996 |
| EP | 0808614 | 11/1997 |
| EP | 0815806 | 1/1998 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7-24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO96/26689 | 2/1996 |
| WO | WO96/21404 | 7/1996 |
| WO | WO96/25124 | 8/1996 |
| WO | WO97/12563 | 4/1997 |
| WO | WO97/12564 | 4/1997 |
| WO | WO 97/14375 | 4/1997 |
| WO | WO 98/32412 | 7/1998 |
| WO | WO 98/47447 | 10/1998 |
| WO | WO 99/07308 | 2/1999 |
| WO | WO99/17680 | 4/1999 |
| WO | WO99/23976 | 5/1999 |
| WO | WO99/38456 | 8/1999 |
| WO | WO99/38458 | 8/1999 |
| WO | WO99/39660 | 8/1999 |
| WO | WO99/39663 | 8/1999 |
| WO | WO99/49928 | 10/1999 |
| WO | WO00/13611 | 3/2000 |
| WO | WO00/18328 | 4/2000 |
| WO | WO00/32241 | 6/2000 |
| WO | WO00/45744 | 8/2000 |
| WO | WO00/53119 | 9/2000 |
| WO | WO01/01885 | 1/2001 |
| WO | WO01/82835 | 11/2001 |
| WO | WO02/26164 | 4/2002 |
| WO | WO02/064061 | 8/2002 |
| WO | WO02/064065 | 8/2002 |
| WO | WO02/094127 | 11/2002 |
| WO | WO03/009779 | 2/2003 |
| WO | WO03/057076 | 7/2003 |
| WO | WO2004/087015 | 10/2004 |
| WO | WO2006/055533 | 5/2006 |
| WO | WO2006/066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |
| WO | WO2009/080326 | 7/2009 |
| WO | WO2009/080327 | 7/2009 |

OTHER PUBLICATIONS

Landers, Rüdiger and Mülhaupt, Rolf "Desktop manufacturing of complex objects, prototypes and biomedical scaffolds by means of computer-assisted design combined with computer-guided 3D plotting of polymers and reactive oligomers" Macromeolecular Materials and Engineering, vol. 282, Issue 1, pp. 17-21, Oct. 2000.
U.S. Appl. No. 09/582,318, Aug. 14, 2002, Office Action.
U.S. Appl. No. 09/582,318, Mar. 7, 2003, Notice of Allowance.
U.S. Appl. No. 09/742,144, Sep. 24, 2002, Office Action.
U.S. Appl. No. 09/742,144, May 14, 2003, Office Action.
U.S. Appl. No. 09/742,144, Aug. 29, 2003, Notice of Allowance.
U.S. Appl. No. 09/916,394, Aug. 12, 2003, Office Action.
U.S. Appl. No. 09/916,394, Oct. 9, 2003, Office Action.
U.S. Appl. No. 09/916,394, Mar. 2, 2004, Office Action.
U.S. Appl. No. 09/967,789, Sep. 17, 2003, Office Action.
U.S. Appl. No. 09/967,789, Feb. 17, 2004, Notice of Allowance.
U.S. Appl. No. 10/241,523, Aug. 18, 2004, Office Action.
U.S. Appl. No. 10/241,523, Oct. 25, 2004, Office Action.
U.S. Appl. No. 10/241,523, Mar. 8, 2005, Office Action.
U.S. Appl. No. 10/241,523, Jun. 3, 2005, Office Action.
U.S. Appl. No. 10/241,523, Aug. 23, 2005, Office Action.
U.S. Appl. No. 10/241,523, Nov. 16, 2005, Office Action.
U.S. Appl. No. 10/241,523, Apr. 27, 2006, Office Action.
U.S. Appl. No. 10/743,857, Mar. 15, 2007, Office Action.
U.S. Appl. No. 10/743,857, Nov. 16, 2007, Office Action.
U.S. Appl. No. 10/743,857, May 8, 2008, Office Action.
U.S. Appl. No. 10/743,857, Jan. 6, 2009, Office Action.
U.S. Appl. No. 10/743,857, May 27, 2009, Office Action.

(56) References Cited

OTHER PUBLICATIONS

U.S. Appl. No. 10/743,857, Feb. 12, 2010, Notice of Allowance.
U.S. Appl. No. 10/743,857, Jun. 25, 2010, Notice of Allowance.
U.S. Appl. No. 10/859,636, Jun. 1, 2007, Office Action.
U.S. Appl. No. 10/859,636, Dec. 31, 2007, Office Action.
U.S. Appl. No. 10/859,636, Apr. 15, 2008, Office Action.
U.S. Appl. No. 10/859,636, Oct. 1, 2008, Notice of Allowance.
U.S. Appl. No. 10/859,636, Mar. 5, 2009, Office Action.
U.S. Appl. No. 10/859,636, Oct. 19, 2009, Notice of Allowance.
U.S. Appl. No. 10/859,636, Feb. 1, 2010, Notice of Allowance.
U.S. Appl. No. 10/859,636, May 19, 2010, Notice of Allowance.
U.S. Appl. No. 10/859,636, Dec. 9, 2010, Notice of Allowance.
U.S. Appl. No. 10/884,613, Mar. 30, 2005, Office Action.
U.S. Appl. No. 10/884,613, Nov. 14, 2005, Office Action.
U.S. Appl. No. 10/903,013, Mar. 15, 2007, Office Action.
U.S. Appl. No. 10/903,013, Nov. 19, 2007, Office Action.
U.S. Appl. No. 10/903,013, May 14, 2008, Office Action.
U.S. Appl. No. 10/903,013, Jan. 5, 2009, Office Action.
U.S. Appl. No. 10/903,013, May 27, 2009, Office Action.
U.S. Appl. No. 10/903,013, Feb. 12, 2010, Notice of Allowance.
U.S. Appl. No. 10/903,013, Jun. 24, 2010, Notice of Allowance.
U.S. Appl. No. 10/903,014, Mar. 15, 2007, Office Action.
U.S. Appl. No. 10/903,014, Nov. 16, 2007, Office Action.
U.S. Appl. No. 10/903,014, May 13, 2008, Office Action.
U.S. Appl. No. 10/903,014, Jan. 13, 2009, Office Action.
U.S. Appl. No. 10/903,014, Jun. 1, 2009, Office Action.
U.S. Appl. No. 10/903,014, Feb. 5, 2010, Notice of Allowance.
U.S. Appl. No. 10/903,014, May 26, 2010, Office Action.
U.S. Appl. No. 10/903,014, Jun. 24, 2010, Notice of Allowance.
U.S. Appl. No. 10/903,080, Mar. 15, 2007, Office Action.
U.S. Appl. No. 10/903,080, Nov. 19, 2007, Office Action.
U.S. Appl. No. 10/903,080, May 12, 2008, Office Action.
U.S. Appl. No. 10/903,080, Dec. 30, 2008, Office Action.
U.S. Appl. No. 10/903,080, May 27, 2009, Office Action.
U.S. Appl. No. 10/903,080, Jan. 13, 2010, Notice of Allowance.
U.S. Appl. No. 10/903,080, Sep. 16, 2010, Notice of Allowance.
U.S. Appl. No. 10/909,117, Aug. 22, 2007, Office Action.
U.S. Appl. No. 10/909,117, May 12, 2008, Office Action.
U.S. Appl. No. 10/909,117, Dec. 30, 2008, Office Action.
U.S. Appl. No. 10/909,117, May 27, 2009, Office Action.
U.S. Appl. No. 10/909,117, Jan. 13, 2010, Notice of Allowance.
U.S. Appl. No. 10/909,117, Sep. 16, 2010, Notice of Allowance.
U.S. Appl. No. 10/909,118, Mar. 29, 2007, Office Action.
U.S. Appl. No. 10/909,118, Nov. 19, 2007, Office Action.
U.S. Appl. No. 10/909,118, May 12, 2008, Office Action.
U.S. Appl. No. 10/909,118, Jan. 5, 2009, Office Action.
U.S. Appl. No. 10/909,118, Jul. 24, 2009, Office Action.
U.S. Appl. No. 10/909,118, Jan. 13, 2010, Notice of Allowance.
U.S. Appl. No. 10/909,118, Sep. 21, 2010, Notice of Allowance.
U.S. Appl. No. 10/954,948, Mar. 15, 2007, Office Action.
U.S. Appl. No. 10/954,948, Nov. 16, 2007, Office Action.
U.S. Appl. No. 10/954,948, May 15, 2008, Office Action.
U.S. Appl. No. 10/954,948, Jan. 13, 2009, Office Action.
U.S. Appl. No. 10/954,948, May 29, 2009, Office Action.
U.S. Appl. No. 10/954,948, Jan. 13, 2010, Notice of Allowance.
U.S. Appl. No. 10/954,948, Jul. 6, 2010, Notice of Allowance.
U.S. Appl. No. 10/955,425, Mar. 15, 2007, Office Action.
U.S. Appl. No. 10/955,425, Nov. 16, 2007, Office Action.
U.S. Appl. No. 10/955,425, May 13, 2008, Office Action.
U.S. Appl. No. 10/955,425, Jan. 13, 2009, Office Action.
U.S. Appl. No. 10/955,425, May 28, 2009, Office Action.
U.S. Appl. No. 10/955,425, Feb. 26, 2010, Notice of Allowance.
U.S. Appl. No. 10/955,425, Jun. 25, 2010, Notice of Allowance.
U.S. Appl. No. 11/313,110, Jan. 8, 2008, Office Action.
U.S. Appl. No. 11/313,110, Jul. 2, 2008, Office Action.
U.S. Appl. No. 11/313,110, Mar. 3, 2009, Office Action.
U.S. Appl. No. 11/313,110, Nov. 2, 2009, Notice of Allowance.
U.S. Appl. No. 11/313,110, Feb. 18, 2010, Notice of Allowance.
U.S. Appl. No. 11/313,110, Jun. 15, 2010, Notice of Allowance.
U.S. Appl. No. 11/404,450, Feb. 4, 2009, Office Action.
U.S. Appl. No. 11/404,450, Mar. 17, 2009, Office Action.
U.S. Appl. No. 11/404,450, Sep. 30, 2009, Office Action.
U.S. Appl. No. 11/404,450, Apr. 22, 2010, Office Action.
U.S. Appl. No. 11/404,450, Nov. 26, 2010, Office Action.
U.S. Appl. No. 11/404,450, Aug. 10, 2011, Office Action.
U.S. Appl. No. 11/404,450, Jan. 31, 2012, Office Action.
U.S. Appl. No. 11/435,260, Jan. 10, 2008, Office Action.
U.S. Appl. No. 11/435,260, Mar. 26, 2008, Office Action.
U.S. Appl. No. 11/435,260, Dec. 16, 2008, Office Action.
U.S. Appl. No. 11/435,260, Jun. 18, 2009, Notice of Allowance.
U.S. Appl. No. 11/435,260, Jun. 26, 2009, Notice of Allowance.
U.S. Appl. No. 11/601,475, Jul. 22, 2008, Office Action.
U.S. Appl. No. 11/601,475, Jan. 6, 2009, Office Action.
U.S. Appl. No. 11/601,475, Jun. 1, 2009, Office Action.
U.S. Appl. No. 11/601,475, Jan. 15, 2010, Notice of Allowance.
U.S. Appl. No. 11/601,475, Jul. 9, 2010, Notice of Allowance.
U.S. Appl. No. 11/731,820, Jan. 27, 2010, Office Action.
U.S. Appl. No. 11/731,820, Aug. 5, 2010, Notice of Allowance.
U.S. Appl. No. 11/731,820, Dec. 16, 2010, Notice of Allowance.
U.S. Appl. No. 11/731,882, Feb. 3, 2010, Office Action.
U.S. Appl. No. 11/731,882, Sep. 1, 2010, Office Action.
U.S. Appl. No. 11/731,882, Aug. 29, 2011, Notice of Allowance.
U.S. Appl. No. 11/732,244, Sep. 28, 2009, Office Action.
U.S. Appl. No. 11/732,244, May 5, 2010, Notice of Allowance.
U.S. Appl. No. 11/732,244, Jun. 21, 2010, Notice of Allowance.
U.S. Appl. No. 11/805,584, Apr. 27, 2009, Office Action.
U.S. Appl. No. 11/805,584, Oct. 29, 2009, Office Action.
U.S. Appl. No. 11/805,584, Mar. 15, 2010, Office Action.
U.S. Appl. No. 11/805,584, Oct. 4, 2010, Office Action.
U.S. Appl. No. 11/805,584, May 12, 2011, Notice of Allowance.
U.S. Appl. No. 11/961,290, May 6, 2009, Office Action.
U.S. Appl. No. 11/961,290, Dec. 18, 2009, Office Action.
U.S. Appl. No. 11/961,290, Aug. 3, 2012, Office Action.
U.S. Appl. No. 11/961,290, Dec. 12, 2012, Office Action.
U.S. Appl. No. 11/961,384, May 26, 2009, Office Action.
U.S. Appl. No. 11/961,384, Oct. 8, 2009, Office Action.
U.S. Appl. No. 11/961,384, Apr. 23, 2012, Office Action.
U.S. Appl. No. 11/961,384, Aug. 21, 2012, Notice of Allowance.
U.S. Appl. No. 11/961,754, Jul. 22, 2009, Office Action.
U.S. Appl. No. 11/961,754, Apr. 5, 2010, Notice of Allowance.
U.S. Appl. No. 11/961,754, Jul. 28, 2010, Notice of Allowance.
U.S. Appl. No. 11/973,707, Jun. 9, 2009, Office Action.
U.S. Appl. No. 11/973,707, Mar. 19, 2010, Office Action.
U.S. Appl. No. 11/973,707, Oct. 12, 2011, Notice of Allowance.
U.S. Appl. No. 11/961,775, Oct. 1, 2009, Office Action.
U.S. Appl. No. 11/961,775, Mar. 31, 2010, Office Action.
U.S. Appl. No. 12/608,335, May 11, 2012, Office Action.
U.S. Appl. No. 12/608,335, Dec. 2, 2013, Office Action.
U.S. Appl. No. 12/608,335, Mar. 3, 2014, Advisory Action.
U.S. Appl. No. 12/875,971, Apr. 19, 2012, Office Action.
U.S. Appl. No. 12/875,971, Jul. 26, 2012, Notice of Allowance.
U.S. Appl. No. 12/895,032, Feb. 1, 2012, Office Action.
U.S. Appl. No. 12/895,032, Jul. 3, 2012, Office Action.
U.S. Appl. No. 12/895,032, Aug. 13, 2013, Office Action.
U.S. Appl. No. 12/895,032, Oct. 29, 2013, Office Action.
U.S. Appl. No. 12/895,032, Mar. 14, 2014, Office Action.
U.S. Appl. No. 12/949,481, Jan. 5, 2012, Office Action.
U.S. Appl. No. 12/949,481, Feb. 15, 2012, Office Action.
U.S. Appl. No. 12/949,481, Aug. 13, 2012, Notice of Allowance.
U.S. Appl. No. 12/966,916, Jun. 10, 2011, Office Action.
U.S. Appl. No. 12/966,916, Jan. 5, 2012, Office Action.
U.S. Appl. No. 12/966,916, May 23, 2012, Notice of Allowance.
U.S. Appl. No. 13/089,039, Oct. 16, 2012, Office Action.
U.S. Appl. No. 13/089,039, Jun. 28, 2013, Office Action.
U.S. Appl. No. 13/089,039, Sep. 26, 2013, Office Action.
U.S. Appl. No. 13/089,039, Apr. 14, 2014, Notice of Allowance.
U.S. Appl. No. 13/411,135, Oct. 16, 2012, Office Action.
U.S. Appl. No. 13/411,135, Mar. 15, 2013, Office Action.
U.S. Appl. No. 13/411,135, Oct. 8, 2013, Office Action.
U.S. Appl. No. 13/411,135, Mar. 14, 2014, Office Action.
U.S. Appl. No. 11/961,290, Aug. 19, 2014, Notice of Allowance.
U.S. Appl. No. 12/608,335, Apr. 9, 2015, Office Action.
U.S. Appl. No. 12/895,032, Jan. 30, 2015, Office Action.

(56) References Cited

OTHER PUBLICATIONS

U.S. Appl. No. 12/895,032, Aug. 13, 2015, Office Action.
U.S. Appl. No. 13/411,135, Oct. 24, 2014, Office Action.
U.S. Appl. No. 13/411,135, Mar. 30, 2015, Office Action.
U.S. Appl. No. 13/411,135, Jan. 15, 2016, Notice of Allowance.
U.S. Appl. No. 13/801,469, Jan. 12, 2016, Office Action.

* cited by examiner

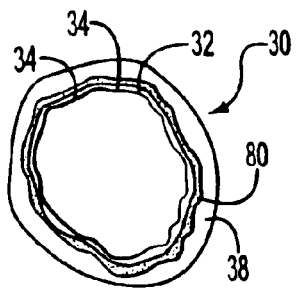
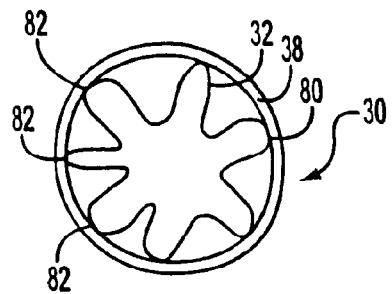
FIG. 14A  FIG. 14B
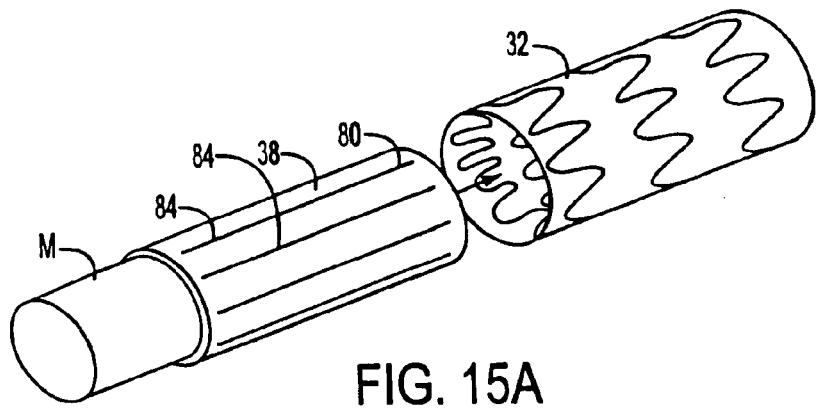
FIG. 15A
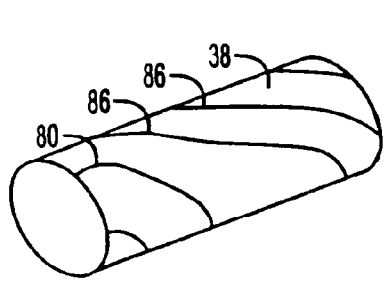
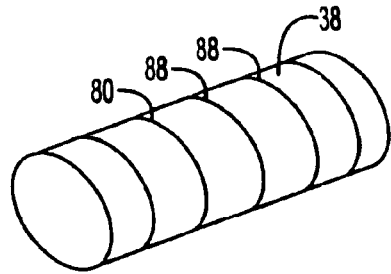
FIG. 15B  FIG. 15C
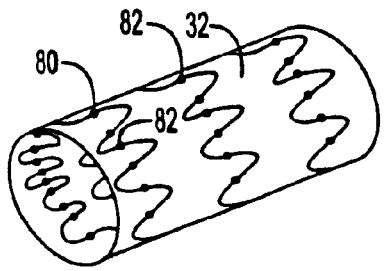
FIG. 15D

METHODS AND APPARATUS FOR STENTING COMPRISING ENHANCED EMBOLIC PROTECTION COUPLED WITH IMPROVED PROTECTIONS AGAINST RESTENOSIS AND THROMBUS FORMATION

REFERENCE TO RELATED APPLICATIONS

This application is a continuation of U.S. patent application Ser. No. 13/089,039, filed Apr. 18, 2011, which is a continuation of U.S. patent application Ser. No. 11/731,820, filed on Mar. 29, 2007, now U.S. Pat. No. 7,927,365, which is a continuation of U.S. patent application Ser. No. 10/859,636, filed on Jun. 3, 2004, now U.S. Pat. No. 7,927,364, which is continuation of U.S. patent application Ser. No. 09/967,789, filed on Sep. 28, 2001, now U.S. Pat. No. 6,755,856, which is a continuation-in-part of U.S. patent application Ser. No. 09/742,144, filed on Dec. 19, 2000, now U.S. Pat. No. 6,682,554, which is a continuation-in-part of U.S. patent application Ser. No. 09/582,318, filed on Jun. 23, 2000, now U.S. Pat. No. 6,602,285, which claims the benefit of the filing date of International Application PCT/EP99/06456, filed on Sep. 2, 1999, which claims priority from German Application 19840645.2, filed on Sep. 5, 1998, the entireties of which are incorporated herein by reference.

BACKGROUND

1. Field of the Invention

The present invention relates to stents, and more particularly, to stent grafts having an expandable web structure configured to provide enhanced embolic protection and reduce restenosis and thrombus formation.

2. Background of the Invention

Stents are commonly indicated for a variety of intravascular and non-vascular applications, including restoration and/or maintenance of patency within a patient's vessel. Stents are also used to reduce restenosis of a blood vessel post-dilation, thereby ensuring adequate blood flow through the vessel. Previously known stents are formed of a cell or mesh structure, having apertures through which endothelial cells migrate rapidly. These endothelial cells form a smooth coating over the stent that limits interaction between the stent and blood flowing through the vessel, thereby minimizing restenosis and thrombus formation.

In many applications, in addition to maintenance of vessel patency and limitation of restenosis, protection against release of embolic material from the walls of the vessel is desired. Emboli released into the bloodstream flow downstream, where they may occlude flow and cause death, stroke, or other permanent injury to the patient. The apertures between adjoining cells of previously known stents may provide an avenue for such embolic release, depending upon the application.

In addition to embolic protection, a smooth surface, i.e. a substantially continuous surface lacking apertures, may be desired to permit unencumbered recrossability with guide wires, balloon catheters, etc., into the lumen of the stent, for example, to compress stenosis or restenosis and open the lumen, to resize the stent to accommodate vascular geometry changes, etc. Further, equalization of forces applied by or to the stent may be desired to reduce a risk of the stent causing vessel dissection. Due to the apertures, previously known stents may provide only limited embolic protection, recrossability, and force distribution in some applications.

A covered stent, or a stent graft, comprises a stent that is at least partially externally-covered, internally-lined, or sintered with a biocompatible material that is impermeable to stenotic emboli. Common covering materials include biocompatible polymers, such as polyethylene terephthalate (PETP or "Dacron") or expanded polytetrafluoroethylene (ePTFE or "Teflon"). Stent grafts may be either balloon-expandable or self-expanding. Balloon-expandable systems may be expanded to an optimal diameter in-vivo that corresponds to the internal profile of the vessel. Upon compression, self-expanding embodiments characteristically return in a resilient fashion to their unstressed deployed configurations and are thus preferred for use in tortuous anatomy and in vessels that undergo temporary deformation.

A stent graft provides embolic protection by sealing emboli against a vessel wall and excluding the emboli from blood flow through the vessel. Additionally, since the biocompatible material of a stent graft closely tracks the profile of the stent, forces applied by and to an impinging vessel wall are distributed over a larger surface area of the stent, i.e. the force is not just applied at discrete points by "struts" located between apertures of the stent. Rather, the biocompatible material also carries the load and distributes it over the surface of the stent. Furthermore, stent grafts provide a smooth surface that allows improved or unencumbered recrossability into the lumen of the graft, especially when the biocompatible material lines the interior of, or is sintered into, the stent.

While the biocompatible materials used in stent grafts are impermeable to, and provide protection against, embolic release, they typically do not allow rapid endothelialization, because they also are impermeable or substantially impermeable to ingrowth of endothelial cells (i.e. have pores smaller than about 30 µm) that form the protective intima layer of blood vessels. These cells must migrate from the open ends of a stent graft into the interior of the stent. Migration occurs through blood flow and through the scaffold provided by the graft. Such migration is slow and may take a period of months, as opposed to the period of days to weeks required by bare (i.e. non-covered) stents.

In the interim, thrombus may form within the lumen of the graft, with potentially dire consequences. As a further drawback, migration of the endothelium through the open ends of a graft may leave the endothelial coating incomplete, i.e. it does not span a mid-portion of the graft. In addition, the endothelial layer is often thicker and more irregular than the endothelialization observed with bare stents, enhancing the risk of restenosis and thrombus formation.

Porous covered stents also are known. For example, U.S. Pat. No. 5,769,884 to Solovay describes a covered stent having porous regions near the end of the stent, wherein the pores are sized to allow tissue ingrowth and endothelialization. The middle region of the stent is described as being much less porous or non-porous, to encapsulate damaged or diseased tissue and inhibit tissue ingrowth.

The Solovay device is believed to have several drawbacks. First, the end regions of the stent are described as having a preferred pore diameter as large as 120 µm. Pore diameters greater than about 100 µm may provide inadequate embolic protection; thus, if the end regions compress a stenosis, hazardous embolization may result. Further, since the middle region of the stent is adapted to inhibit tissue ingrowth, endothelial cells must migrate into the middle region of the stent from the end regions and from blood flow. As discussed previously, such migration is slow and provides an inferior endothelial layer.

An additional drawback to previously known devices is that many are not configured for use at a vessel bifurcation. A bare stent placed across a vessel side branch is expected to disrupt flow into the side branch and create turbulence that may lead to thrombus formation. Conversely, placement of a non-porous covered stent/stent graft across the bifurcation is expected to permanently exclude the side branch from blood flow, because such grafts are substantially impermeable to blood.

In view of the drawbacks associated with previously known stents and stent grafts, it would be desirable to provide apparatus and methods for stenting that overcome the drawbacks of previously known devices.

It further would be desirable to provide methods and apparatus that reduce the risk of embolic release, while also reducing the risk of restenosis and thrombus formation.

It also would be desirable to provide apparatus and methods for stenting that allow improved recrossability into the lumen of the apparatus.

It would be desirable to provide apparatus and methods for stenting that distribute forces applied by or to the apparatus.

It still further would be desirable to provide apparatus and methods suitable for use in bifurcated vessels.

SUMMARY OF THE INVENTION

In view of the foregoing, it is an object of the present invention to provide apparatus and methods for stenting that overcome the drawbacks of previously known apparatus and methods.

It is an object to reduce the risk of embolic release during and after stenting, and also reduce the risk of restenosis and thrombus formation.

It is yet another object of the present invention to provide apparatus and methods that allow unencumbered recrossability into the lumen of the apparatus.

It is an object to provide apparatus and methods for stenting that distribute forces applied by or to the apparatus.

It is an object to provide apparatus and methods suitable for use in a bifurcated vessel.

These and other objects of the present invention are accomplished by providing apparatus comprising a stent, for example, a balloon-expandable, a self-expanding, a bistable cell, or a metal mesh stent. A biocompatible material at least partially is sintered between the apertures of the stent, or covers the interior or exterior surface (or both) of the stent. Unlike previously known stent grafts, embodiments of the present invention are both permeable to ingrowth and impermeable to release of critical-sized emboli along their entire lengths. Thus, the present invention provides the embolic protection, force distribution, and improved recrossability characteristic of non-porous stent grafts, while further providing the protection against restenosis and thrombus formation characteristic of bare stents.

In one preferred embodiment, the biocompatible material of the present invention comprises, for example, a porous woven, knitted, or braided material having pore sizes determined as a function of the tightness of the weave, knit, or braid. Pore size is selected to allow endothelial cell ingrowth, while preventing release of emboli larger than a predetermined size. In an alternative embodiment, the biocompatible material comprises pores that are chemically, physically, mechanically, laser-cut, or otherwise created through the material with a specified diameter, spacing, etc. The pores may be provided with uniform or non-uniform density, size, and/or shape. The pores preferably have a minimum width large enough to promote endothelial cell ingrowth, and a maximum width small enough to reduce the risk of embolic release.

Apparatus also is provided for use in a bifurcated or branched vessel. Since the porous biocompatible material of the present invention is permeable to blood flow, it is expected that, when implanted, flow into a side branch will continue uninterrupted. The small diameter of the pores, relative to the diameter of the stent apertures, will provide a grating that is expected to minimize turbulence and allow thrombus-free blood flow into the side branch. Optionally, the porosity, i.e. the diameter, density, shape, and/or arrangement, of the pores may be altered in the region of the side branch to ensure adequate flow.

Alternatively, the stent and biocompatible material may comprise a radial opening. When stenting at a vessel bifurcation or branching, the radial opening may be positioned in line with the side branch to maintain patency of the branch. Alternatively, a plurality of radial openings may be provided along the length of the implant to facilitate continuous blood flow through a plurality of side branches.

Stents for use with apparatus of the present invention preferably comprise a tubular body with a wall having a web structure configured to expand from a contracted delivery configuration to an expanded deployed configuration. The web structure comprises a plurality of neighboring web patterns having adjoining webs. Each web has three sections: a central section arranged substantially parallel to the longitudinal axis in the contracted delivery configuration, and two lateral sections coupled to the ends of the central section. The angles between the lateral sections and the central section increase during expansion, thereby reducing or substantially eliminating length decrease of the stent due to expansion, while increasing a radial stiffness of the stent.

Preferably, each of the three sections of each web is substantially straight, the lateral sections preferably define obtuse angles with the central section, and the three sections are arranged relative to one another to form a concave or convex structure. When contracted to its delivery configuration, the webs resemble stacked or nested bowls or plates. This configuration provides a compact delivery profile, as the webs are packed against one another to form web patterns resembling rows of the stacked plates.

Neighboring web patterns are preferably connected to one another by connection elements preferably formed as straight sections. In a preferred embodiment, the connection elements extend between adjacent web patterns from the points of interconnection between neighboring webs within a given web pattern.

The orientation of connection elements between a pair of neighboring web patterns preferably is the same for all connection elements disposed between the pair. However, the orientation of connection elements alternates between neighboring pairs of neighboring web patterns. Thus, a stent illustratively flattened and viewed as a plane provides an alternating orientation of connection elements between the neighboring pairs: first upwards, then downwards, then upwards, etc.

As will be apparent to one of skill in the art, positioning, distribution density, and thickness of connection elements and adjoining webs may be varied to provide stents exhibiting characteristics tailored to specific applications. Applications may include, for example, use in the coronary or peripheral (e.g. renal) arteries. Positioning, density, and thickness may even vary along the length of an individual stent in order to vary flexibility and radial stiffness characteristics along the length of the stent.

Stents for use with apparatus of the present invention preferably are flexible in the delivery configuration. Such flexibility beneficially increases a clinician's ability to guide the stent to a target site within a patient's vessel. Furthermore, stents of the present invention preferably exhibit high radial stiffness in the deployed configuration Implanted stents therefore are capable of withstanding compressive forces applied by a vessel wall and maintaining vessel patency. The web structure described hereinabove provides the desired combination of flexibility in the delivery configuration and radial stiffness in the deployed configuration. The combination further may be achieved, for example, by providing a stent having increased wall thickness in a first portion of the stent and decreased wall thickness with fewer connection elements in an adjacent portion or portions of the stent.

Embodiments of the present invention may comprise a coating or attached active groups configured for localized delivery of radiation, gene therapy, medicaments, thrombin inhibitors, or other therapeutic agents. Furthermore, embodiments may comprise one or more radiopaque features to facilitate proper positioning within a vessel.

Methods of using the apparatus of the present invention also are provided.

BRIEF DESCRIPTION OF THE DRAWINGS

Further features of the invention, its nature and various advantages, will be more apparent from the following detailed description of the preferred embodiments, taken in conjunction with the accompanying drawings, in which like reference numerals apply to like parts throughout, and in which:

FIGS. 14A and 14B are cross-sectional views, illustrating stent/stent covering attachment schemes; and FIGS. 15A-15D are isometric schematic views illustrating various techniques for attaching a stent covering to a stent in a manner that provides the attachment scheme of FIG. 14B.

DETAILED DESCRIPTION OF THE INVENTION

The present invention relates to stent grafts having an expandable web structure, the stent grafts being configured to provide enhanced embolic protection and improved protection against restenosis and thrombus formation. These attributes are attained by attaching to a stent a biocompatible material that is impermeable to emboli but permeable to ingrowth of endothelial cells. Attaching the material to the stent also distributes forces applied to or by the apparatus, and facilitates recrossing into the lumen of the apparatus post-implantation with guide wires, balloons, etc. Thus, unlike previously known bare stents, the present invention provides improved protection against embolic release, a smoother surface for recrossing, and better distribution of forces applied to or by the apparatus. Moreover, unlike previously known, non-porous stent grafts, the present invention provides enhanced protection against thrombus formation and restenosis via rapid endothelialization.

Figure 1:
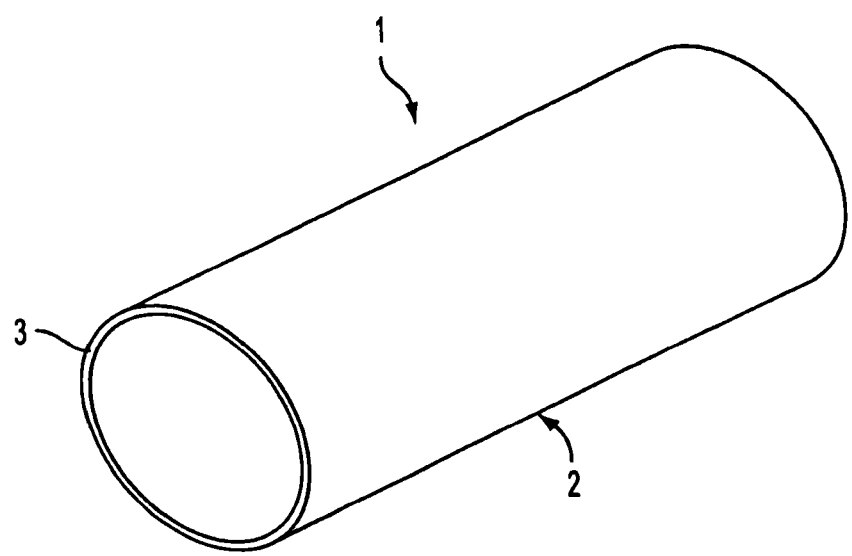
FIG. 1 is a schematic isometric view illustrating the basic structure of a preferred stent for use with apparatus of the present invention.

Prior to a detailed presentation of embodiments of the present invention, preferred stent designs for use with such embodiments are provided in FIGS. 1-5. Stent 1 of FIG. 1 is as described in co-pending U.S. patent application Ser. No. 09/742,144, filed Dec. 19, 2000, which is incorporated herein by reference. Stent 1 comprises tubular flexible body 2 having wall 3. Wall 3 comprises a web structure described hereinbelow with respect to FIGS. 2-5.

Stent 1 and its web structure are expandable from a contracted delivery configuration to an expanded deployed configuration. Depending on the material of fabrication, stent 1 may be either self-expanding or expandable using a balloon catheter. If self-expanding, the web structure is preferably fabricated from a superelastic material, such as a nickel-titanium alloy. Furthermore, stent 1 preferably is fabricated from biocompatible and/or biodegradable materials. It also may be radiopaque to facilitate delivery, and it may comprise an external coating that, for example, retards thrombus formation or restenosis within a vessel. The coating alternatively may deliver therapeutic agents into the patient's blood stream.

Figure 2:
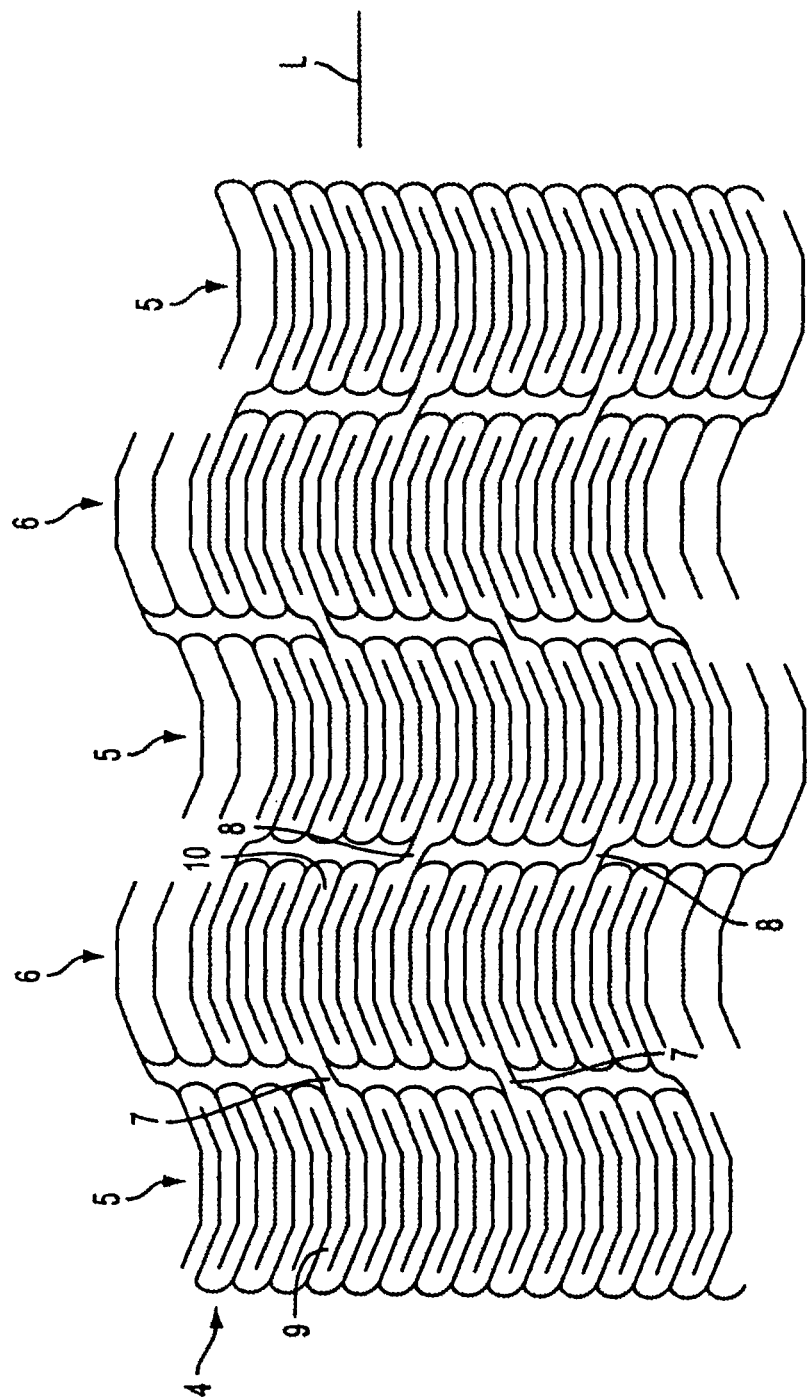
FIG. 2 is a schematic view illustrating a web structure of a wall of the stent of FIG. 1 in a contracted delivery configuration.
Figure 3:
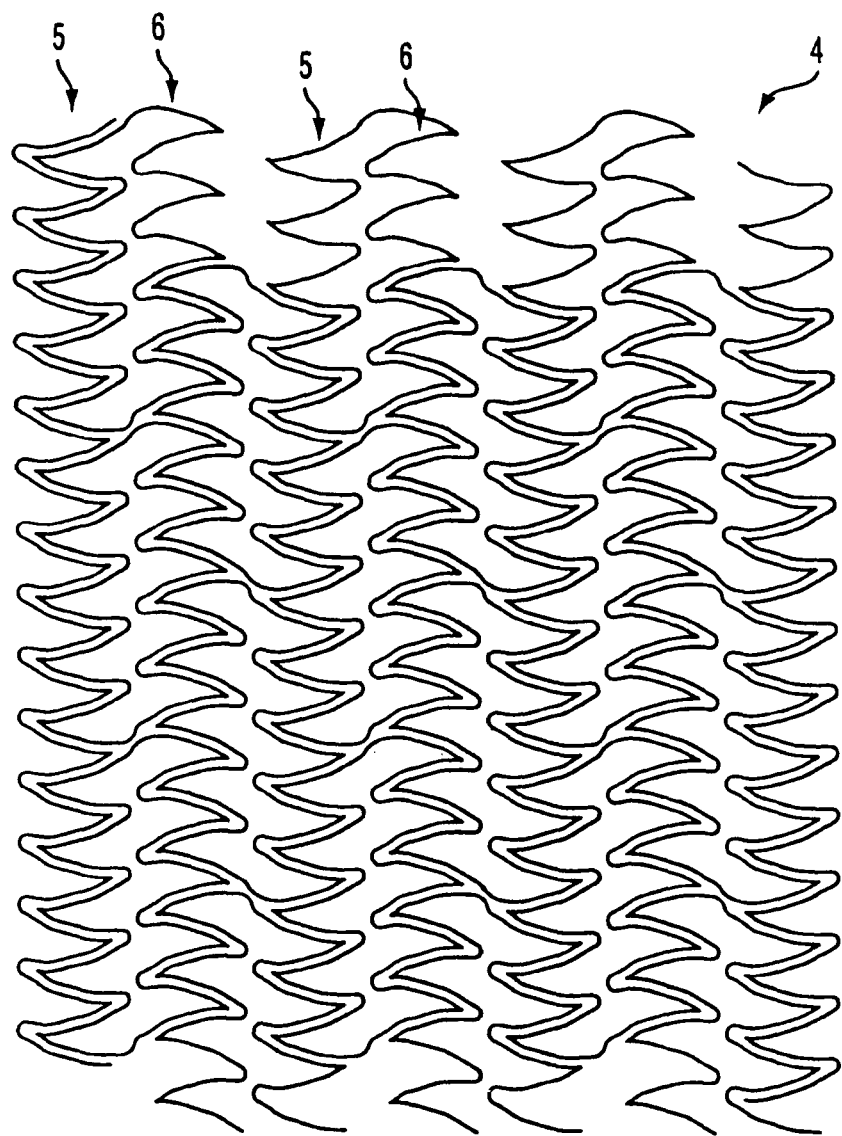
FIG. 3 is a schematic view illustrating the web structure of the stent of FIG. 1 in an expanded deployed configuration.
Figure 4:
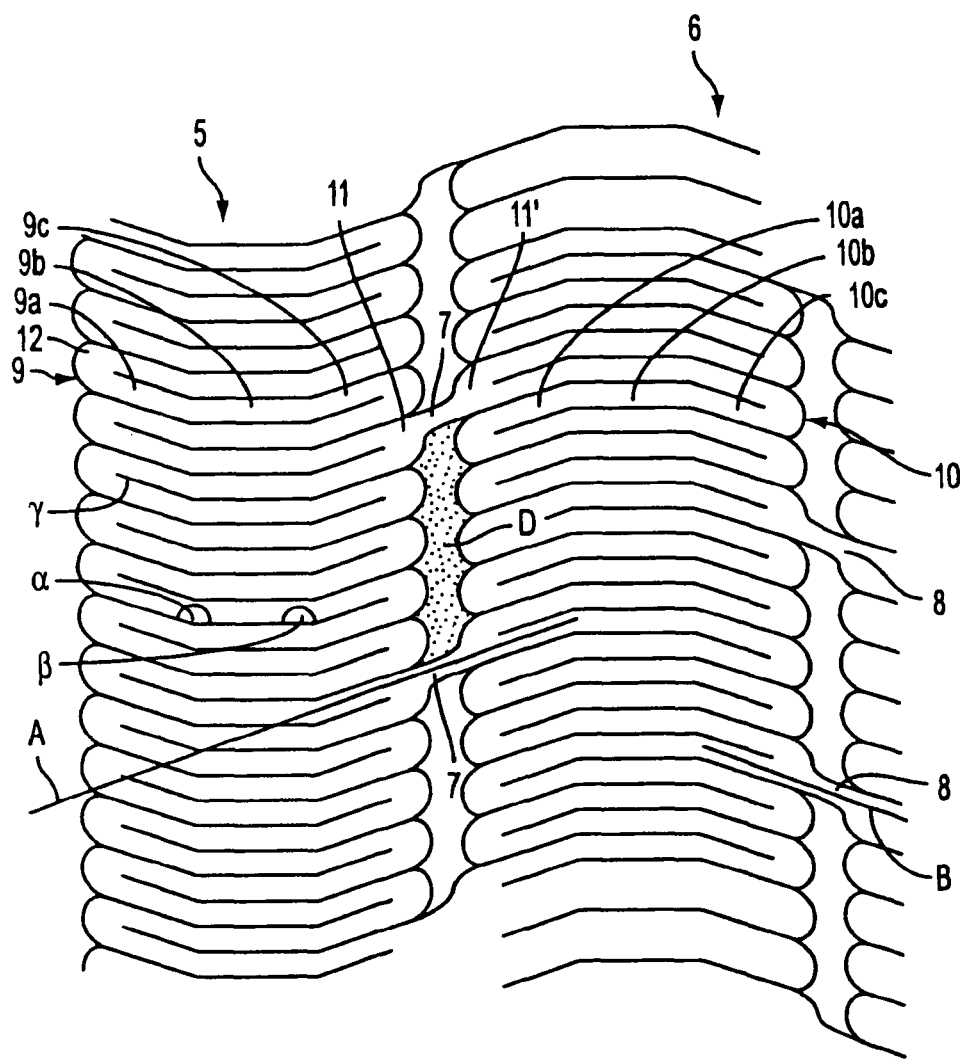
FIG. 4 is an enlarged schematic view of the web structure in the delivery configuration.

With reference to FIGS. 2-4, a first embodiment of the web structure of stent 1 is described. In FIGS. 2-4, wall 3 of body 2 of stent 1 is shown flattened into a plane for illustrative purposes. FIG. 2 shows web structure 4 in a contracted delivery configuration, with line L indicating the longitudinal axis of the stent. Web structure 4 comprises neighboring web patterns 5 and 6 arranged in alternating, side-by-side fashion. Thus, the web patterns seen in FIG. 2 are arranged in the sequence 5, 6, 5, 6, 5, etc.

FIG. 2 illustrates that web patterns 5 comprise adjoining webs 9 (concave up in FIG. 2), while web patterns 6 comprise adjoining webs 10 (convex up in FIG. 2). Each of these webs has a concave or convex shape resulting in a stacked plate- or bowl-like appearance when the stent is contracted to its delivery configuration. Webs 9 of web patterns 5 are rotated 180 degrees with respect to webs 10 of web patterns 6, i.e., alternating concave and convex shapes. The structure of webs 9 and 10 is described in greater detail herein below with respect to FIG. 4.

Neighboring web patterns 5 and 6 are interconnected by connection elements 7 and 8. A plurality of connection elements 7 and 8 are provided longitudinally between each pair of web patterns 5 and 6. Multiple connection elements 7 and 8 are disposed in the circumferential direction between adjacent webs 5 and 6. The position, distribution density, and thickness of these pluralities of connection elements may be varied to suit specific applications in accordance with the present invention.

Connection elements 7 and 8 exhibit opposing orientation. However, all connection elements 7 preferably have the same orientation that, as seen in FIG. 2, extends from the left side, bottom, to the right side, top. Likewise, all connection elements 8 preferably have the same orientation that extends from the left side, top, to the right side, bottom. Connection elements 7 and 8 alternate between web patterns 5 and 6, as depicted in FIG. 2.

FIG. 3 illustrates the expanded deployed configuration of stent 1, again with reference to a portion of web structure 4. When stent 1 is in the expanded deployed configuration, web structure 4 provides stent 1 with high radial stiffness. This stiffness enables stent 1 to remain in the expanded configuration while, for example, under radial stress. Stent 1 may experience application of radial stress when, for example, implanted into a hollow vessel in the area of a stenosis.

FIG. 4 is an enlarged view of web structure 4 detailing a portion of the web structure disposed in the contracted delivery configuration of FIG. 2. FIG. 4 illustrates that each of webs 9 of web pattern 5 comprises three sections 9a, 9b and 9c, and each of webs 10 of web pattern 6 comprises three sections 10a, 10b and 10c. Preferably, each individual section 9a, 9b, 9c, 10a, 10b and 10c, has a straight configuration.

Each web 9 has a central section 9b connected to lateral sections 9a and 9c, thus forming the previously mentioned bowl- or plate-like configuration. Each adjoining web 9 has a substantially uniform length. Sections 9a and 9b enclose obtuse angle .alpha. Likewise, central section 9b and lateral section 9c enclose obtuse angle .beta. Sections 10a-10c of each web 10 of each web pattern 6 are similarly configured, but are rotated 180 degrees with respect to corresponding webs 9. Where two sections 9a or 9c, or 10a or 10c adjoin one another, third angle .gamma. is formed this angle is zero where the stent is in the fully contracted position, as shown in FIG. 4).

Preferably, central sections 9b and 10b are substantially aligned with the longitudinal axis L of the tubular stent, when the stent is in the contracted delivery configuration. The angles between the sections of each web increase in magnitude during expansion to the deployed configuration, except that angle .gamma., which is initially zero or acute, approaches a right angle after deployment of the stent. This increase provides high radial stiffness with reduced shortening of the stent length during deployment. As will of course be understood by one of ordinary skill in the art, the number of adjoining webs that span a circumference of the stent preferably is selected corresponding to the vessel diameter in which the stent is to be implanted.

FIG. 4 illustrates that, with stent 1 disposed in the contracted delivery configuration, webs 9 adjoin each other in an alternating fashion and are each arranged like plates stacked into one another, as are adjoining webs 10. FIG. 4 further illustrates that the configuration of the sections of each web applies to all of the webs, which jointly form web structure 4 of wall 3 of tubular body 2 of stent 1. Webs 9 are interconnected within each web pattern 5 via rounded connection sections 12, of which one connection section 12 is representatively labeled. Webs 10 of each neighboring web pattern 6 are similarly configured.

FIG. 4 also once again demonstrates the arrangement of connection elements 7 and 8. Connection elements 7, between a web pattern 5 and a neighboring web pattern 6, are disposed obliquely relative to the longitudinal axis L of the stent with an orientation A, which is the same for all connection elements 7. Orientation A is illustrated by a straight line that generally extends from the left side, bottom, to the right side, top of FIG. 4. Likewise, the orientation of all connection elements 8 is illustrated by line B that generally extends from the left side, top, to the right side, bottom of FIG. 4. Thus, an alternating A, B, A, B, etc., orientation is obtained over the entirety of web structure 4 for connection elements between neighboring web patterns.

Connection elements 7 and 8 are each configured as a straight section that passes into a connection section 11 of web pattern 5 and into a connection section 11' of web pattern 6. This is illustratively shown in FIG. 4 with a connection element 7 extending between neighboring connection sections 11 and 11', respectively. It should be understood that this represents a general case for all connection elements 7 and 8.

Since each web consists of three interconnected sections that form angles .alpha. and .beta. with respect to one another, which angles are preferably obtuse in the delivery configuration, expansion to the deployed configuration of FIG. 3 increases the magnitude of angles .alpha. and .beta. This angular increase beneficially provides increased radial stiffness in the expanded configuration. Thus, stent 1 may be flexible in the contracted delivery configuration to facilitate delivery through tortuous anatomy, and also may exhibit sufficient radial stiffness in the expanded configuration to ensure vessel patency, even when deployed in an area of stenosis. The increase in angular magnitude also reduces and may even substantially eliminate length decrease of the stent due to expansion, thereby decreasing a likelihood that stent 1 will not completely span a target site within a patient's vessel post-deployment.

The stent of FIG. 4 is particularly well suited for use as a self-expanding stent when manufactured, for example, from a shape memory alloy such as nickel-titanium. In this case, web patterns 5 and 6 preferably are formed by laser-cutting a tubular member, wherein adjacent webs 9 and 10 are formed using slit-type cuts. Only the areas circumferentially located between connection members 7 and 8 (shaded area D in FIG. 4) require removal of areas of the tubular member. These areas also may be removed from the tubular member using laser-cutting techniques.

Figure 5:
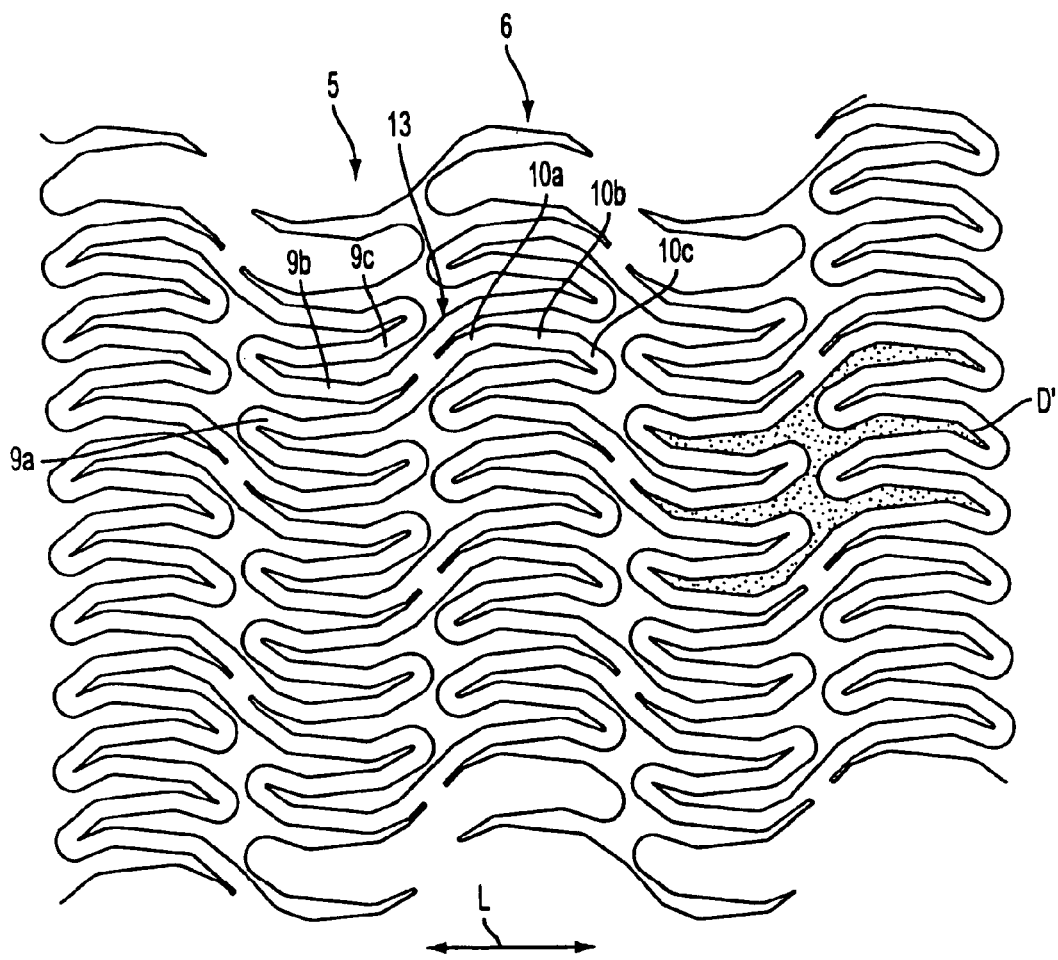
FIG. 5 is a schematic view of an alternative web structure of the stent of FIG. 1 having transition sections and shown in an as-manufactured configuration.

Referring now to FIG. 5, an alternative embodiment of the web structure of stent 1 is described. FIG. 5 shows the alternative web structure in an as-manufactured configuration. The basic pattern of the embodiment of FIG. 5 corresponds to that of the embodiment of FIGS. 2-4. Thus, this alternative embodiment also relates to a stent having a tubular flexible body with a wall having a web structure that is configured to expand from a contracted delivery configuration to a deployed configuration.

Likewise, the web structure again comprises a plurality of neighboring web patterns, of which two are illustratively labeled in FIG. 5 as web patterns 5 and 6. Web patterns 5 and 6 are again provided with adjoining webs 9 and 10, respectively. Each of webs 9 and 10 is subdivided into three sections, and reference is made to the discussion provided hereinabove, particularly with respect to FIG. 4. As will of course be understood by one of skill in the art, the stent of FIG. 5 will have a smaller diameter when contracted (or crimped) for delivery, and may have a larger diameter than illustrated in FIG. 5 when deployed (or expanded) in a vessel.

The embodiment of FIG. 5 differs from the previous embodiment by the absence of connection elements between web patterns. In FIG. 5, web patterns are interconnected to neighboring web patterns by transition sections 13, as shown by integral transition section 13 disposed between sections 9c and 10c. Symmetric, inverted web patterns are thereby obtained in the region of transition sections 13. To enhance stiffness, transition sections 13 preferably have a width greater than twice the width of webs 9 or 10.

As seen in FIG. 5, every third neighboring pair of webs 9 and 10 is joined by an integral transition section 13. As will be clear to those of skill in the art, the size and spacing of transition sections 13 may be altered in accordance with the principles of the present invention.

An advantage of the web structure of FIG. 5 is that it provides stent 1 with compact construction coupled with a high degree of flexibility in the delivery configuration and high load-bearing capabilities in the deployed configuration. Furthermore, FIG. 5 illustrates that, as with connection elements 7 and 8 of FIG. 4, transition sections 13 have an alternating orientation and are disposed obliquely relative to the longitudinal axis of the stent (shown by reference line L). FIG. 5 also illustrates that, especially in the deployed configuration, an H-like configuration of transition sections 13 with adjoining web sections is obtained.

The stent of FIG. 5 is well suited for use as a balloon-expandable stent, and may be manufactured from stainless steel alloys. Unlike the stent of FIG. 4, which is formed in the contracted delivery configuration, the stent of FIG. 5 preferably is formed in a partially deployed configuration by removing the shaded areas D' between webs 9 and 10 using laser-cutting or chemical etching techniques. In this case, central sections 9b and 10b are substantially aligned with the longitudinal axis L of the stent when the stent is crimped onto the dilatation balloon of a delivery system.

As will be apparent to one of skill in the art, positioning, distribution density, and thickness of connection elements and adjoining webs may be varied to provide stents exhibiting characteristics tailored to specific applications. Applications may include, for example, use in the coronary or peripheral (e.g. renal) arteries. Positioning, density, and thickness may even vary along the length of an individual stent in order to flexibility and radial stiffness characteristics along the length of the stent.

Stents of the present invention preferably are flexible in the delivery configuration. Such flexibility beneficially increases a clinician's ability to guide the stent to a target site within a patient's vessel. Furthermore, stents of the present invention preferably exhibit high radial stiffness in the deployed configuration. Implanted stents therefore are capable of withstanding compressive forces applied by a vessel wall and maintain vessel patency. The web structure described hereinabove provides the desired combination of flexibility in the delivery configuration and radial stiffness in the deployed configuration. The combination further may be achieved, for example, by providing a stent having increased wall thickness in a first portion of the stent and decreased wall thickness with fewer connection elements in an adjacent portion or portions of the stent.

Figure 6A:
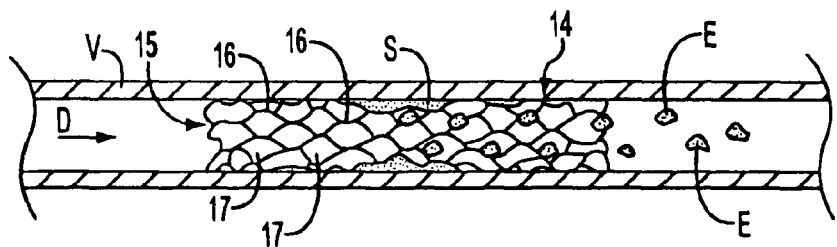
FIGS. 6A-6C are side-sectional views of a prior art bare stent in an expanded deployed configuration within a patient's vasculature, illustrating limitations of bare stents with regard to embolic protection, recrossability, and force distribution, respectively.
Figure 6B:
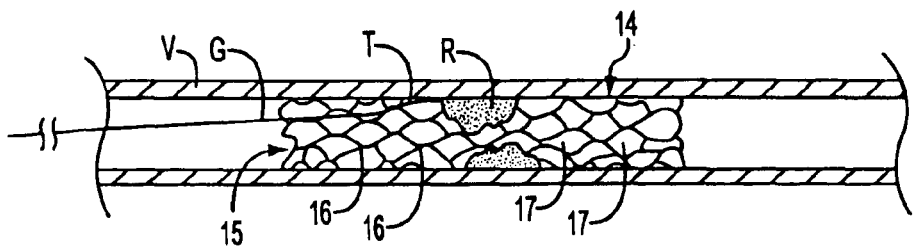
Figure 6C:
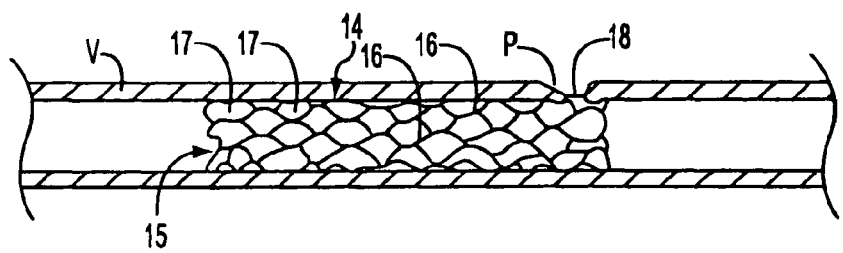
Figure 7:
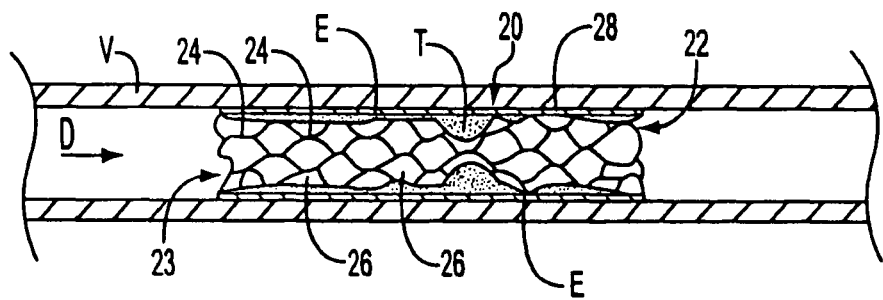
FIG. 7 is a side-sectional view of a prior art, non-porous stent graft in an expanded deployed configuration within a patient's vasculature, illustrating the potential for thrombus formation and restenosis due to inefficient endothelial cell migration.

Referring now to FIGS. 6 and 7, limitations of previously known apparatus are described prior to the detailed description of embodiments of the present invention. In FIGS. 6A-6C, limitations of a previously known bare stent are described. As seen in FIG. 6A, stent 14 has been implanted within a patient's vessel V at a treatment site exhibiting stenosis S, using well-known techniques. Stent 14 has lumen 15 and comprises cell or mesh structure 16 having apertures 17. Stent 14 is shown expanded, e.g. either resiliently or via a balloon, to compress stenosis S against the wall of vessel V and restore patency within the vessel. During compression of stenosis S, particles break away from the stenosis to form emboli E. These emboli escape from the vessel wall through apertures 17 of stent 14. Blood flowing through vessel V in direction D carries the released emboli E downstream, where the emboli may occlude flow and cause death, stroke, or other permanent injury to the patient. Stent 14 therefore may provide inadequate embolic protection, depending upon the specific application.

In FIG. 6B, stent 14 has been implanted for an extended period of time in vessel V across a stenosed region. Restenosis R has formed within lumen 15 of stent 14, requiring further reintervention to restore patency to the vessel. Apertures 17 of stent 14 provide the stent with a non-uniform surface that complicates recrossing of the stent with guide wires, angioplasty balloons, etc., post-implantation.

In FIG. 6B, guide wire G has been advanced through the patient's vasculature into lumen 15 of stent 14 to provide a guide for advancement of an angioplasty balloon to compress restenosis R and reopen vessel V. Distal tip T of guide wire G has become entangled within structure 16 of stent 14 during recrossing, because the wire has inadvertently passed through an aperture 17. If guide wire G becomes caught on structure 16, emergency surgery may be necessary to remove the guide wire. Alternatively, a portion of guide wire G (or a portion of any other device inserted post-implantation through lumen 15 and entangled within stent 14) may break off from the guide wire and remain within the vessel, presenting a risk for thrombus formation or vessel dissection.

In addition to the problems associated with recrossing bare stent 14 upon restenosis, if stent 14 is self-expanding, the stent may provide inadequate radial force to compress a vessel stenosis at the time of implantation (not shown). Recrossing lumen 15 of stent 14 with a balloon catheter then may be necessary to compress the stenosis and fully open the lumen (not shown). As illustrated in FIG. 6B, such recrossing may be difficult or impossible.

In FIG. 6C, stent 14 has been implanted into vessel V that is subject to temporary deformation, for example, due to contact with neighboring muscles, due to joint motion, or due to external pressure applied to the vessel. The wall of vessel V impinges on a single strut 18 of structure 16 of stent 14. Since all force is concentrated at the point of impingement of vessel V and strut 18, strut 18 punctures vessel V at site P. Alternatively, temporary deformation of vessel V may kink stent 14 at strut 18, thus reducing lumen 15 and decreasing the utility of stent 14 (not shown). Clearly, either of these conditions may create a serious risk to the health of the patient. Similarly, stent 10 may dissect the vessel wall or may kink if implanted in tortuous anatomy (not shown). It would therefore be desirable to modify stent 14 to better distribute loads applied to the stent.

Referring now to FIG. 7, limitations of a previously known, non-porous covered stent, or stent graft, are described. Stent graft 20 comprises balloon-expandable or self-expanding stent 22 having lumen 23. Stent 22 comprises cell or mesh structure 24 having apertures 26. The stent is covered with biocompatible material 28, which commonly comprises a biocompatible polymer, such as PTFE, PETP, or a homologic material. Biocompatible material 28 is beneficially impermeable to stenotic emboli, but detrimentally impermeable to endothelial cell ingrowth.

In FIG. 7, graft 20 has been implanted for an extended period of time, for example, a period of months, within vessel V. Unlike stent 14 of FIG. 6, endothelial cells are not able to rapidly migrate through apertures 26 of stent 22 and surround graft 20 with a thin, uniform layer of endothelial cells that limit interaction between the graft and blood flowing through the vessel, thereby reducing restenosis and thrombus formation. Rather, since biocompatible material 28 is impermeable to ingrowth of the endothelial cells that form the protective intima layer of blood vessels, these cells must migrate from the open ends of graft 20 into the interior of lumen 23.

Migration occurs via blood flowing through vessel V in direction D and via the scaffold provided by the body of graft 20. However, this migration is slow and may take a period of months, as opposed to the period of days to weeks required for endothelialization of bare stents. Furthermore, as illustrated by endothelial layer E in FIG. 7, migration through the open ends of graft 20 may provide an incomplete endothelial layer, i.e. a layer that does not span a mid-portion of the graft. Layer E also may be thicker and more irregular than the endothelial layer obtained with bare stents. Gaps, irregularity, and thickening in layer E, as well as extended time required for formation of layer E, may yield thrombus T or restenosis within lumen 23 of graft 20, with potentially dire consequences. Stent graft 20 therefore may not provide adequate protection against restenosis and thrombus formation.

Figure 8A:
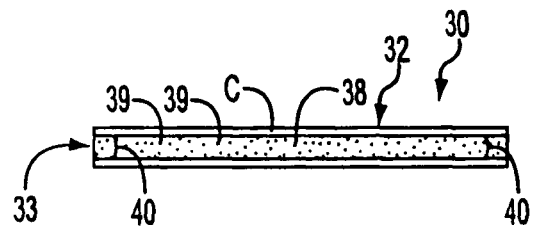
FIGS. 8A and 8B are side-sectional views of a first embodiment of apparatus of the present invention, shown, respectively, in a collapsed delivery configuration and in a deployed configuration.
Figure 8B:
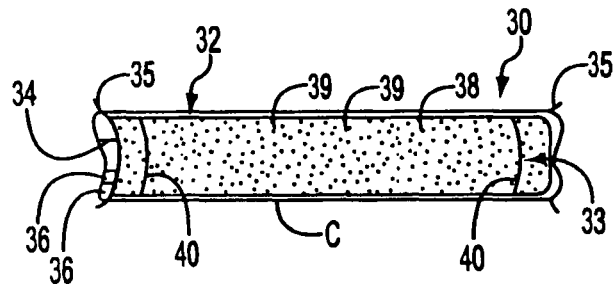

Referring now to FIGS. 8A and 8B, a first embodiment of apparatus of the present invention is described in detail. Apparatus 30 comprises stent 32 having lumen 33. Stent 32 may be, for example, self-expanding or balloon-expandable, or may be of bistable cell or metal mesh construction. Stent 32 comprises cell or mesh structure 34 with apertures 36. In a preferred embodiment, stent 32 comprises the design of stent 1, described hereinabove with respect to FIGS. 1-5. Stent 32 may further comprise an anchoring feature, such as hook or barb 35, to facilitate attachment to a vessel wall. The anchoring feature alternatively may comprise structure 34, which interacts with the vessel wall, for example, by pressing against the wall or by endothelial cell ingrowth into the structure, to anchor stent 32. Biocompatible material 38 having pores 39 is attached to at least a portion of stent 32.

Unlike material 28 of stent graft 20 (and unlike the material described hereinabove with respect to U.S. Pat. No. 5,769,884 to Solovay), material 38 of apparatus 30 is both permeable to endothelial cell ingrowth and impermeable to release of emboli of predetermined size, e.g. larger than about 100 μm, along its entire length. Thus, like stent graft 20 of FIG. 7, apparatus 30 provides enhanced embolic protection, improved force distribution, and improved recrossability; furthermore, like bare stent 14 of FIG. 6, apparatus 30 provides enhanced protection against restenosis and thrombus formation.

Biocompatible material 38 may comprise a biocompatible polymer, for example, a modified thermoplastic Polyurethane, polyethylene terephthalate, polyethylene tetraphthalate, expanded polytetrafluoroethylene, polypropylene, polyester, Nylon, polyethylene, polyurethane, or combinations thereof. Alternatively, biocompatible material 38 may comprise a homologic material, such as an autologous or non-autologous vessel. Further still, material 38 may comprise a biodegradable material, for example, polylactate or polyglycolic acid. In FIG. 8, material 38 illustratively lines the interior surface of stent 32, but it should be understood that material 38 alternatively may cover the stent's exterior surface, may be sintered within apertures 36 of stent 32, or may otherwise be attached to the stent.

Material 38 preferably comprises a woven, knitted, or braided material, wherein the size of pores 39 is determined as a function of the tightness of the weave, knit, or braid. The size of pores 39 then may be specified to allow endothelial cell ingrowth, while preventing release of emboli larger than a critical dangerous size, for example, larger than about 100 .mu.m. In an alternative embodiment, the biocompatible material comprises pores 39 that are chemically, physically, mechanically, or laser cut, or otherwise created through material 38 with a specified diameter, spacing, etc.

Pores 39 may be provided with uniform or non-uniform density, size, and/or shape. The pores preferably have a minimum width no smaller than approximately 30 μm and a maximum width no larger than approximately 100 μm. Widths smaller than about 3 μm are expected to inhibit endothelial cell ingrowth, while widths larger than about 100 μm are expected to provide inadequate embolic protection, i.e. emboli of dangerous size may be released into the blood stream. Each of pores 39 is even more preferably provided with a substantially uniform, round shape having a diameter of approximately 80 μm. Pores 39 preferably are located along the entire length of material 38.

Stent 32 may be fabricated from a variety of materials. If self-expanding, the stent preferably comprises a superelastic material, such as a nickel-titanium alloy, spring steel, or a polymeric material. Alternatively, stent 32 may be fabricated with a resilient knit or wickered weave pattern of elastic materials, such as stainless steel. If balloon-expandable, metal mesh, or bistable cell, stent 32 is preferably fabricated from elastic materials, such as stainless steel or titanium.

At least a portion of stent 32 preferably is radiopaque to facilitate proper positioning of apparatus 30 within a vessel. Alternatively, apparatus 30, or a delivery system for apparatus 30 (see FIG. 9), may comprise a radiopaque feature, for example, optional radiopaque marker bands 40, to facilitate positioning. Marker bands 40 comprise a radiopaque material, such as gold or platinum.

Apparatus 30 also may comprise coatings or attached active groups C configured for localized delivery of radiation, gene therapy, medicaments, thrombin inhibitors, or other therapeutic agents. Coatings or active groups C may, for example, be absorbed or adsorbed onto the surface, may be attached physically, chemically, biologically, electrostatically, covalently, or hydrophobically, or may be bonded to the surface through Van der Waal's forces, or combinations thereof, using a variety of techniques that are well-known in the art.

In FIG. 8A, apparatus 30 is shown in a collapsed delivery configuration, while, in FIG. 8B, apparatus 30 is in an expanded deployed configuration. If stent 32 is self-expanding, apparatus 30 may be collapsed to the delivery configuration over a guide wire or elongated member, and then covered with a sheath to maintain the apparatus in the delivery configuration. Using well-known percutaneous techniques, apparatus 30 is advanced through a patient's vasculature to a treatment site, where the sheath is withdrawn; stent 32 dynamically self-expands to the deployed configuration of FIG. 8B (see FIG. 9). If stent 32 is balloon expandable, apparatus 30 may be mounted in the delivery configuration on a balloon catheter, for delivery to the treatment site. Upon delivery using well-known techniques, the balloon catheter is inflated with sufficient pressure to facilitate irreversible expansion of the apparatus to the deployed configuration (not shown).

With reference to FIGS. 9A-9D, a method of using the apparatus of FIG. 8 within a patient's vasculature is described in detail. In FIG. 9, stent 32 of apparatus 30 is illustratively self-expanding. However, it should be understood that stent 32 alternatively may be, for example, balloon-expandable, or be made from bistable cells or a metal mesh, in accordance with the present invention.

Figure 9A:
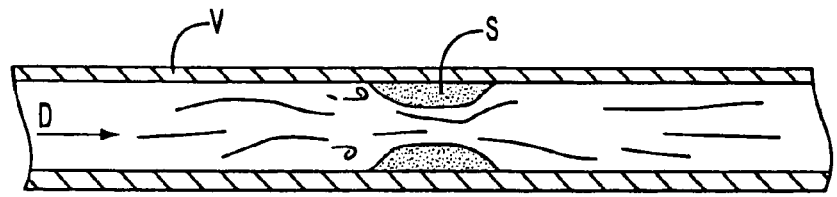
FIGS. 9A-9D are side-sectional views of the apparatus of FIGS. 8A-8B within a patient's vasculature, illustrating a method of using the apparatus in accordance with the present invention.
Figure 9B:
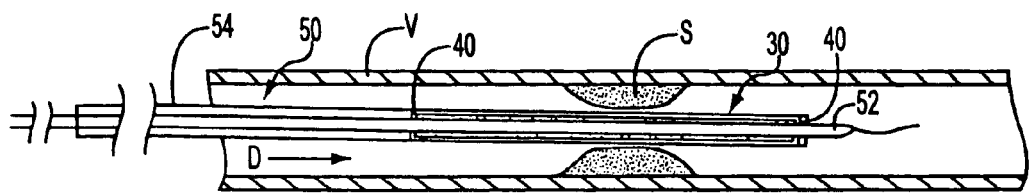

In FIG. 9A, vessel V is partially occluded with stenosis S that disrupts blood flow in direction D. Using well-known techniques, apparatus 30, disposed in the collapsed delivery configuration over elongated member 52 and constrained in that configuration by sheath 54 of delivery system 50, is advanced to the point of stenosis, as seen in FIG. 9B. Radiopacity of stent 32, viewed under a fluoroscope, may facilitate proper positioning of apparatus 30 within the vessel. Alternatively, radiopaque marker bands 40, illustratively disposed on sheath 54, may facilitate positioning.

Figure 9C:
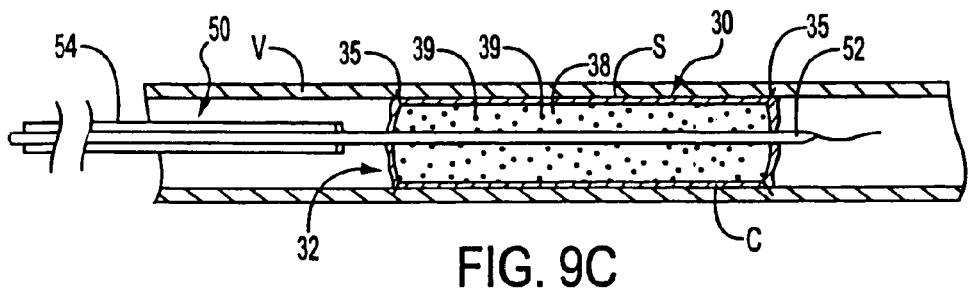

In FIG. 9C, sheath 54 is retracted proximally with respect to elongated member 52, thereby allowing apparatus 30 to dynamically self-expand to the deployed configuration. Apparatus 30 compresses and traps stenosis S against the wall of vessel V. Optional barb or hook 35 of stent 32 facilitates anchoring of stent 32 to vessel V. The controlled size of pores 39 along the length of apparatus 30 ensures that dangerous emboli, broken away from stenosis S during compression, do not escape from the vessel wall and enter the bloodstream. Apparatus 30 protects against embolization at the time of implantation, and further protects against delayed stroke caused by late embolization.

Figure 9D:
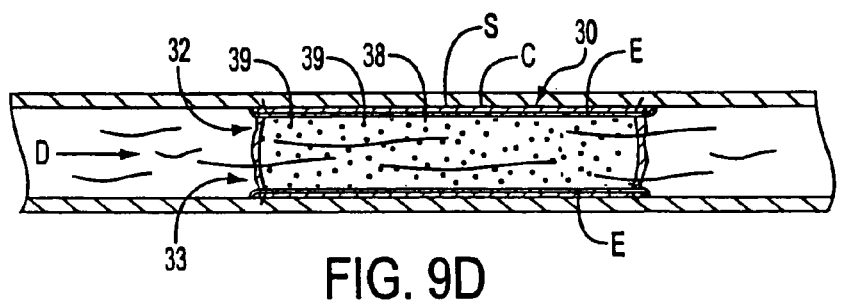

As seen in FIG. 9D, delivery system 50 is removed from the vessel. Pores 39 allow endothelial cells to rapidly migrate through apertures 36 of stent 32 and into the interior of apparatus 30 to form endothelial layer E over the entirety of apparatus 30. Layer E forms, for example, over a period of days to weeks. Unlike the endothelial layer covering stent graft 20 in FIG. 7, endothelial layer E of apparatus 30 is expected to form rapidly, to be complete, thin, and substantially regular. Layer E acts as a protective layer that reduces adverse interaction between apparatus 30 and the patient, thereby lessening the risk of thrombus formation and restenosis. Thus, in addition to maintaining patency of vessel V, apparatus 30 provides embolic protection coupled with reduced likelihood of restenosis and thrombus formation. Furthermore, optional coating or attached active groups C of material 38 may deliver radiation, gene therapy, medicaments, thrombin inhibitors, or other therapeutic substances to the vessel wall, or directly into the blood stream.

Apparatus 30 compresses and seals stenosis S against the wall of vessel V, thereby preventing embolic material from the stenosis from traveling downstream. Alternatively, via angioplasty or other suitable means, stenosis S may be compressed against the vessel wall prior to insertion of apparatus 30, in which case apparatus 30 still protects against delayed stroke caused by late embolization. In addition to the application of FIG. 9, apparatus 30 may be used for a variety of other applications, including, but not limited to, bridging defective points within a vessel, such as aneurysms, ruptures, dissections, punctures, etc.

While the rapid endothelialization of apparatus 30, discussed with respect to FIG. 9D, minimizes risk of restenosis and thrombus formation, restenosis may still occur in a limited number of patients. Additionally, vessel V may become lax and expand to a larger diameter. Under these and other circumstances, it may be necessary to recross lumen 33 of apparatus 30 with interventional instruments. These instruments may, for example, adjust apparatus 30, restore patency to vessel V in an area of restenosis, treat vascular complications distal to apparatus 30, or facilitate any of a variety of other minimally invasive procedures.

Figure 10A:
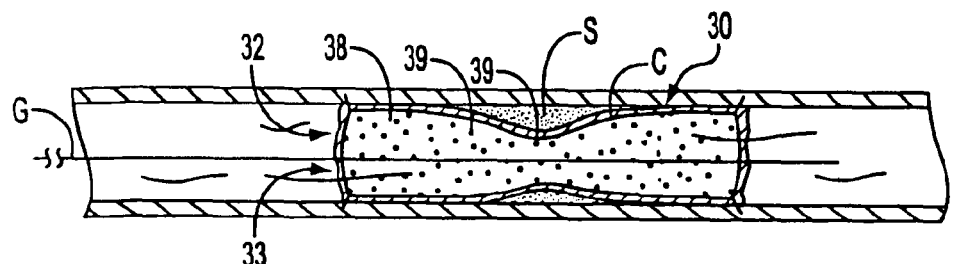
FIGS. 10A-10C are side-sectional views of the apparatus of FIGS. 8A-8B within a patient's vasculature, illustrating capacity for reintroduction into the lumen of the apparatus and a method for establishing or restoring vessel patency after implantation of the apparatus.
Figure 10B:
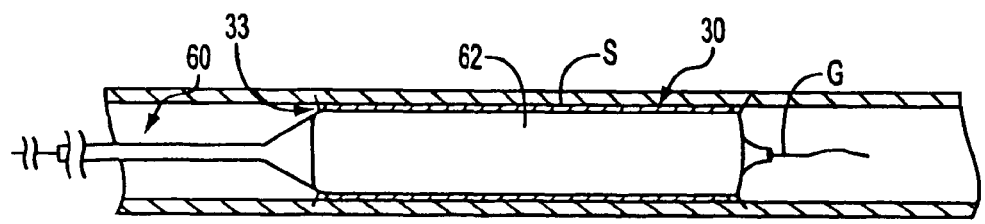
Figure 10C:
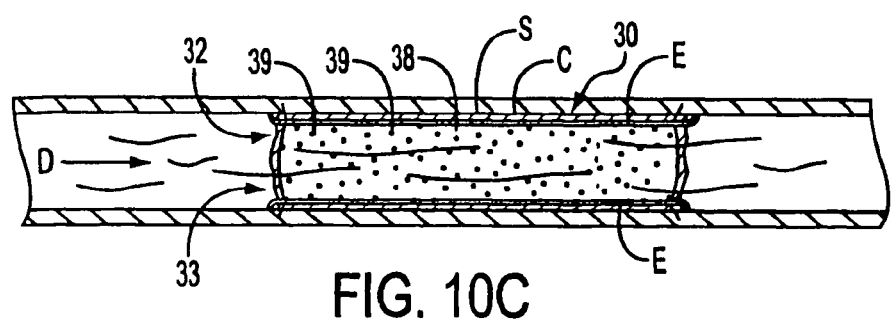

Referring now to FIGS. 10A-10C, capacity for recrossing with apparatus 30 is described. As in FIGS. 9A-9D, stent 32 of apparatus 30 is illustratively self-expandable. In FIG. 10A, stent 32 has been implanted in vessel V using the techniques described hereinabove with respect to FIGS. 9A-9C. However, in contrast to FIG. 9C, stent 32 comprises insufficient radial strength to fully compress and seal stenosis S against the wall of vessel V. Guide wire G is therefore advanced through lumen 33 to provide a guide for advancement of a balloon catheter to fully compress stenosis S. The smooth interior surface provided by biocompatible material 38 of apparatus 30 ensures that guide wire G may recross lumen 33 without becoming entangled in the stent, as was described hereinabove with respect to FIG. 6B.

In FIG. 10B, once guide wire G has recrossed lumen 33, balloon catheter 60 is advanced over guide wire G to the point of stenosis S. Balloon 62 of catheter 60 is inflated with sufficient pressure to compress stenosis S against the walls of vessel V and fully deploy apparatus 30. As seen in FIG. 10C, balloon 62 is then deflated, and catheter 60 is removed from vessel V, thereby restoring patency to the vessel. Endothelial layer E then rapidly forms via endothelial cells that migrate through apertures 36 of stent 32 and pores 39 of material 38 into the interior of apparatus 30.

As will be apparent to those of skill in the art, recrossing of apparatus 30 may be indicated in a variety of applications, in addition to those of FIG. 10. For example, apparatus 30 may be recrossed in order to compress restenosis that has formed within the vessel, as illustrated with bare stent 14 in FIG. 6B. Additionally, apparatus 30 may be recrossed in order to resize the apparatus so that it conforms to, or accommodates changes in, vessel geometry.

Figure 11:
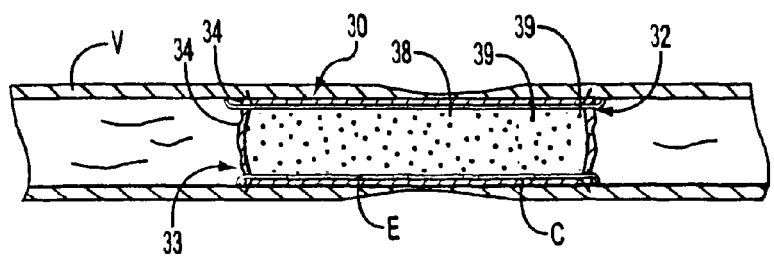
FIG. 11 is a side-sectional view of the apparatus of FIGS. 8A-8B within a patient's vasculature illustrating force distribution upon interaction with an impinging vessel.

With reference now to FIG. 11, apparatus 30 has been implanted into vessel V that is undergoing temporary deformation, for example, due to contact with neighboring muscles, due to joint motion, or due to external pressure applied to the vessel. The wall of vessel V impinges on apparatus 30. In contrast to bare stent 14 of FIG. 6C, apparatus 30 distributes the load applied by vessel V across adjoining cells of structure 34 of stent 32, and across the section of biocompatible material 38 attached to the adjoining cells. Thus, the constricted portion of vessel V neither collapses within lumen 33 of apparatus 30 nor is punctured by apparatus 30. Additionally, since the load is distributed, stent 32 of apparatus 30 does not kink, and lumen 33 remains patent. Similarly, apparatus 30 is expected to continue to function safely and properly if implanted in tortuous anatomy.

Figure 12:
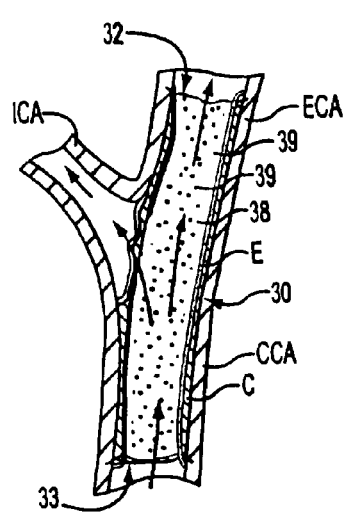
FIG. 12 is a side-sectional view of the apparatus of FIGS. 8A-8B in use at a vessel branching.

Referring to FIG. 12, apparatus 30 is shown in use in a branched or bifurcated vessel. Using well-known techniques, apparatus 30 has been expanded to the deployed configuration within common carotid artery CCA and external carotid artery ECA. Internal carotid artery ICA branches off from the common carotid. Uninterrupted and unimpeded blood flow through the side branch presented by internal carotid artery ICA must be maintained when stenting in the common carotid artery CCA and external carotid artery ECA. Since pores 39 of biocompatible material 38 render apparatus 30 permeable to blood flow, continued blood flow into internal carotid artery ICA is expected to continue. Optionally, the diameter, density, shape and/or packing arrangement of pores 39 may be selectively altered in the region of the vessel branching to ensure that adequate blood continues into the side branch.

Bare stents implanted at a vessel bifurcation may disrupt flow and create areas of stagnation susceptible to thrombus formation. Moreover, bare stents may provide inadequate embolic protection in some applications. The small diameter of pores 39, as compared to the diameter of apertures 36 of stent 32, provides a grating that is expected to reduce turbulence and allow thrombus-free blood flow into the side branch.

Figure 13:
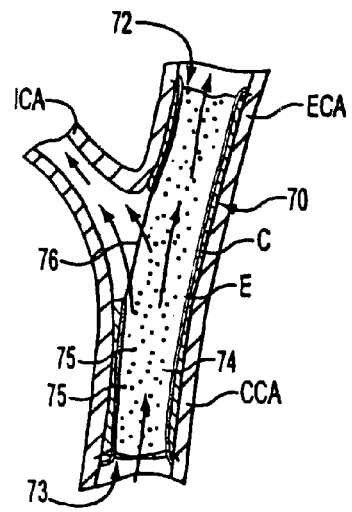
FIG. 13 is a side-sectional view of an alternative embodiment of apparatus of the present invention comprising a radial opening, in use at a vessel branching.

Referring now to FIG. 13, an alternative embodiment of the present invention is shown in use at a vessel bifurcation. Apparatus 70 is similar to apparatus 30 of FIGS. 8-12, except that apparatus 70 comprises radial opening 76 that is expected to allow unimpeded blood flow to a vessel side branch at the point of stenting. Apparatus 70 comprises balloon-expandable or self-expanding stent 72 having lumen 73. Preferably, at least a portion of stent 72 is radiopaque. Biocompatible material 74 having pores 75 is attached to stent 72. Radial opening 76 extends through stent 72 and material 74, thereby providing a side path for blood flow out of lumen 73.

Pores 75 of material 74 are sized such that apparatus 70 is impermeable to stenotic emboli larger than a predetermined size, but is permeable to rapid ingrowth of endothelial cells. Pores 75 preferably have a minimum width of approximately 30 µm and a maximum width of approximately 100 µm, and even more preferably have an average width of about 80 µm. Also, apparatus 70 may optionally comprise coating or attached active groups C, as discussed hereinabove with respect to apparatus 30.

In FIG. 13, apparatus 70 has been expanded to a deployed configuration within common carotid artery CCA and external carotid artery ECA. Prior to expansion of apparatus 70, radial opening 76 was aligned with internal carotid artery ICA to ensure uninterrupted and unimpeded blood flow through the side branch. In addition to maintenance of flow, apparatus 70 provides enhanced embolic protection, facilitates rapid endothelialization, and reduces the risk of restenosis and thrombus formation.

Prior to expansion of apparatus 70, radiopacity of stent 72, or other radiopaque features associated with apparatus 70, may facilitate the alignment of opening 76 with the side branch. Alternatively, Intravascular Ultrasound ("IVUS") techniques may facilitate imaging and alignment. In this case, the delivery catheter for apparatus 70 also may comprise IVUS capabilities, or an IVUS catheter may be advanced into the vessel prior to expansion of apparatus 70 (not shown). Magnetic Resonance Imaging ("MRI") or Optical Coherence Tomography ("OCT"), as well as other imaging modalities that will be apparent to those of skill in the art, alternatively may be used.

Additional embodiments of the present invention may be provided with a plurality of radial openings configured for use in vessels exhibiting a plurality of branchings. The present invention is expected to be particularly indicated for use in the carotid and femoral arteries, although embodiments also may find utility in a variety of other vessels, including the coronary and aortic arteries, and in non-vascular lumens, for example, in the biliary ducts, the respiratory system, or the urinary tract.

With reference now to FIGS. 14 and 15, exemplary techniques for manufacturing apparatus 30 of the present invention are provided. Other techniques within the scope of the present invention will be apparent to those of skill in the art.

Biocompatible material 38 preferably comprises a modified thermoplastic polyurethane, and even more preferably a siloxane modified thermoplastic polyurethane. The material preferably has a hardness in the range of about 70A to 60D, and even more preferably of about 55D. Other materials and hardnesses will be apparent to those of skill in the art. Material 38 preferably is formed by a spinning process (not shown), for example, as described in U.S. Pat. No. 4,475,972 to Wong, which is incorporated herein by reference. Material 38 is heated to form a viscous liquid solution that is placed in a syringe. The material is advanced by a piston or plunger through a fine nozzle, where the material flows out onto a rotating mandrel as fine fibers. The fine fibers form a fibrous mat or covering of biocompatible covering material 38 on the rotating mandrel. As material 38 cools, the fibers solidify, and adjacent, contacting fibers are sintered to one another. Controlling the number of layers of fiber that are applied to the rotating mandrel provides control over the porosity of material 38.

If material 38 is to be sintered to stent 32, this may be achieved by disposing the stent over the mandrel prior to laying down material 38 (not shown). Material 38 also may be attached to either the internal or external surface of stent 32. FIGS. 14 and 15 provide various attachment schemes for attaching material 38 to a surface of the stent.

In FIG. 14A, stent 32 is attached with adhesive 80 to material 38 along all or most of structure 34 of stent 32. Adhesive 80 may comprise, for example, a material similar to biocompatible material 38, but with a different melting point. For example, adhesive 80 may comprise a modified thermoplastic polyurethane with a hardness of about 80A. Stent 32 is dipped in the adhesive and dried. Then, stent 32 and material 38 are coaxially disposed about one another, and the composite apparatus is heated to a temperature above the melting point of adhesive 80, but below the melting point of biocompatible material 38. The composite apparatus is then cooled, which fuses material 38 to stent 32, thereby forming apparatus 30.

A drawback of the attachment scheme of FIG. 14A is that the quantity of adhesive used in forming apparatus 30 may add a significant amount of material to the apparatus, which may increase its delivery profile and/or its rigidity. Additionally, a risk may exist of adhesive particles coming loose during collapse or expansion of apparatus 30. If released within a patient's vasculature, these particles may act as emboli.

FIG. 14B provides an alternative attachment scheme. Material 38 is attached with adhesive 80 to stent 32 at discrete points 82, or is attached along defined planes, such as circumferential bands, longitudinal seams, or helical seams (see FIG. 15). Such attachment reduces the amount of adhesive material required, which, in turn, may reduce rigidity, delivery profile, and a risk of embolization of adhesive particles.

Referring to FIGS. 15A-15D, various techniques for attaching a stent covering to a stent, in a manner that provides the attachment scheme of FIG. 14B, are provided. In FIGS. 15A-15C, biocompatible material 38 is configured for disposal along an interior surface of stent 32. Obviously, the material may alternatively be prepared for disposal about an exterior surface of the stent.

In FIG. 15A, biocompatible material 38 has been formed on mandrel M. Material 38 then is coated with longitudinal seams 84 of adhesive 80, and stent 32 is loaded over the material. Adhesive 80 bonds stent 32 to material 38 along seams 84. In FIG. 15B, material 38 is provided with helical seams 86 of adhesive 80, while in FIG. 15C, material 38 is provided with circumferential bands 88 of adhesive 80. In FIG. 15D, stent 32 is provided with adhesive 80 at discrete points 82. Points 82 may be on either the internal or external surface of stent 32, and biocompatible material 38 then is loaded onto to either the internal or external surface respectively. Additional adhesive configurations will be apparent to those of skill in the art.

While preferred illustrative embodiments of the present invention are described hereinabove, it will be apparent to those of skill in the art that various changes and modifications may be made therein without departing from the invention. The appended claims are intended to cover all such changes and modifications that fall within the true spirit and scope of the invention.

We claim:

1. Apparatus for stenting comprising:
a balloon-expandable stent having proximal and distal ends, and a lumen extending therebetween, a tubular body with a wall having a web structure configured for expansion from a collapsed delivery configuration to an expanded deployed configuration;
the web structure comprising a plurality of interconnected, neighboring web patterns, each web pattern having a plurality of adjoining webs, each adjoining web consisting essentially of a central section interposed between first and second lateral sections, each adjoining web has a substantially uniform length,
wherein within each adjoining web the first lateral sections joins the central section at a first obtuse angle less than 180°, and the second lateral section joins the central section at a second obtuse angle less than 180°, and in the expanded deployed configuration each central section has a longitudinal axis disposed at an oblique angle relative to a longitudinal axis of the tubular body of the stent, longitudinal axes of adjacent central sections, circumferentially disposed about a web pattern of the plurality of web patterns, intersect, and adjacent ones of the neighboring web patterns, adjacently disposed along the longitudinal axis of the tubular body of the stent, have alternating concavity;
a biocompatible material layer, the biocompatible material layer including a material and attached to at least a portion of the stent between the proximal and distal ends, the biocompatible material layer comprising pores along its entire length, the pores having a uniform size,
wherein the biocompatible material layer is attached to the stent along discrete points or defined planes, and wherein the biocompatible material layer comprises a porous woven, knitted or braided material.

2. The apparatus of claim 1, wherein along its length the pores of the biocompatible material layer are dimensioned for enabling endothelial cell in-growth while preventing passage of emboli larger than a predetermined size.

3. The apparatus of claim 2, wherein the pores comprise a minimum width of no less than approximately 30 µm, thereby reducing a risk of restenosis and thrombus formation; wherein the pores comprise a maximum width of no more than approximately 100 µm, thereby enhancing embolic protection.

4. The apparatus of claim 2, wherein the pores are configured to allow blood flow through the pores.

5. The apparatus of claim 1, wherein the web structure defining apertures, the pores of the biocompatible material layer being smaller than the apertures of the web structure.

6. The apparatus of claim 5, wherein the web structure comprises a resilient weave pattern.

7. The apparatus of claim 1, wherein the material chosen from the group consisting of biocompatible polymers, modified thermoplastic Polyurethane, Polyethylene Terephthalate, Polyethylene Tetraphthalate, expanded Polytetrafluoroethylene, Polypropylene, Polyester, Nylon, Polyethylene, Polyurethane, homologic materials, autologous vein, non-autologous vein, biodegradable materials, Polylactate, Polyglycolic Acid, and combinations thereof.

8. The apparatus of claim 1,
wherein the material is disposed on at least an exterior surface portion of the stent; or
wherein the material is disposed on at least an interior surface portion of the stent; or
wherein the material is sintered into apertures of at least a portion of the stent; or
wherein the apparatus is configured to distribute forces applied by or to the apparatus across a portion of the apparatus; or
wherein the apparatus is configured for recrossing of the lumen of the stent when the stent is in the expanded deployed configuration.

9. The apparatus of claim 1, wherein the stent comprises a deformable material.

10. Apparatus for stenting comprising:
a balloon-expandable stent comprising a tubular body with a wall having a web structure configured for expansion from a collapsed delivery configuration to an expanded deployed configuration and having proximal and distal ends, and a lumen extending therebetween;
the web structure comprising a plurality of interconnected, neighboring web patterns, each web pattern having a plurality of adjoining webs, each adjoining web comprising a central section interposed between first and second lateral sections,
wherein within each adjoining web the first lateral section joins the central section at a first obtuse angle less than 180°, and the second lateral section joins the central section at a second obtuse angle less than 180°, and in the expanded deployed configuration each central section has a longitudinal axis disposed at an oblique angle relative to a longitudinal axis of the tubular body of the stent, longitudinal axes of adjacent central sections, circumferentially disposed about a web pattern of the plurality of web patterns, intersect, and adjacent ones of the neighboring web patterns, adjacently disposed along the longitudinal axis of the tubular body of the stent, have alternating concavity; and
a biocompatible material layer, the biocompatible material layer made from a material and attached to at least a portion of the stent only along discrete points or defined planes, wherein the biocompatible material layer comprises a porous woven, knitted or braided material, the biocompatible material layer comprising pores having a substantially uniform, round shape and a substantially uniform size.

11. The apparatus of claim 10, wherein the material comprises pores along its entire length, the pores having diameters larger than approximately 30 µm and smaller than approximately 100 µm;
  wherein the biocompatible material layer comprising pores dimensioned for enabling endothelial cell in-growth while preventing passage of emboli larger than a predetermined size.

12. The apparatus of claim 11, wherein the defined planes are chosen from the group consisting of longitudinal seams, helical seams, and circumferential bands.

13. The apparatus of claim 10, wherein the web structure defining apertures, the pores of the biocompatible material layer being smaller than the apertures of the web structure.

14. The apparatus of claim 10, wherein the material is chosen from the group consisting of bio compatible polymers, modified thermoplastic Polyurethane, Polyethylene Terephtalate, Polyethylene Tetraphthalate, expanded Polytetrafluoroethylene, Polypropylene, Polyester, Nylon, Polyethylene, Polyurethane, homologic materials, autologous vein, non-autologous vein, biodegradable materials, Polylactate, Polyglycolic Acid, and combinations thereof.

15. The apparatus of claim 10,
  wherein the material is disposed on at least an exterior surface portion of the stent; or
  wherein the material is disposed on at least an interior surface portion of the stent; or
  wherein the material is sintered into apertures of at least a portion of the stent; or
  wherein the apparatus is configured to distribute forces applied by or to the apparatus across a portion of the apparatus; or
  wherein the apparatus is configured for recrossing of the lumen of the stent when the stent is in the expanded deployed configuration.

16. The apparatus of claim 10, wherein the apparatus comprises at least one opening configured to be positioned at a vessel side branch; or
  wherein the apparatus further comprises a coating disposed on the material wherein the coating comprises a therapeutic agent configured for release when introduced into a body lumen.

17. Apparatus for stenting comprising:
  a stainless steel, balloon-expandable stent having proximal and distal ends, and a lumen extending therebetween, the stent having a tubular body with a wall having a web structure configured for expansion from a delivery configuration to an expanded deployed configuration;
  the web structure comprising a plurality of interconnected, neighboring web patterns, each web pattern having a plurality of adjoining webs, each adjoining web comprising a central section interposed between first and second lateral sections,
  wherein within each adjoining web the first lateral sections joins the central section at a first obtuse angle less than 180°, and the second lateral section joins the central section at a second obtuse angle less than 180°, and in the expanded deployed configuration each central section has a longitudinal axis disposed at an oblique angle relative to a longitudinal axis of the tubular body of the stent, longitudinal axes of adjacent central sections, circumferentially disposed about a web pattern of the plurality of web patterns, intersect, and adjacent ones of the neighboring web patterns, adjacently disposed along the longitudinal axis of the tubular body of the stent, have alternating concavity; and
  a biocompatible material layer of Polyethylene Tetraphthalate, the biocompatible material being attached to an exterior surface of the stent, along its length the biocompatible material layer comprises pores, wherein the biocompatible material layer comprises a porous woven, knitted or braided material, the pores having a uniform size, the pore size being determined as a function of the tightness of the woven, knitted, or braided material; and
  at least one radiopaque feature located at or near the distal and/or proximal ends of the stent.

18. The apparatus of claim 17, wherein the diameter of the pores are smaller than apertures of the stent.

19. The apparatus of claim 18, wherein the pores are dimensioned for enabling endothelial cell in-growth while preventing passage of emboli larger than a predetermined size.

20. The apparatus of claim 18, wherein the pores have diameters larger than approximately 30 µm and smaller than approximately 100 µm.

* * * * *